United States Patent [19]
Savakis et al.

[11] Patent Number: 5,840,865
[45] Date of Patent: *Nov. 24, 1998

[54] EUKARYOTIC TRANSPOSABLE ELEMENT

[75] Inventors: Charalambos Savakis, Heraklion, Greece; Gerald H. Franz, Baden, Austria; Athanasios Loukeris, Athens, Greece

[73] Assignee: Institute of Molecular Biology and Biotechnology/FORTH, Crete, Greece

[*] Notice: The term of this patent shall not extend beyond the expiration date of Pat. No. 5,348,874.

[21] Appl. No.: 530,566

[22] Filed: Sep. 20, 1995

Related U.S. Application Data

[60] Continuation-in-part of Ser. No. 239,765, May 9, 1994, which is a division of Ser. No. 946,237, Sep. 14, 1992, Pat. No. 5,348,874.

[51] Int. Cl.$^6$ .................................................. C07H 21/04
[52] U.S. Cl. ...................... 536/23.2; 435/196; 435/69.1; 435/172.3; 530/350; 536/23.1; 536/23.5; 935/9; 935/19
[58] Field of Search .................................... 435/196, 69.1, 435/70.1, 172.3, 240.2; 530/350; 536/27.1, 23.1, 23.2, 23.5; 935/9, 19

[56] References Cited

U.S. PATENT DOCUMENTS 5,348,874  9/1994  Savakis et al. ......................... 435/196

OTHER PUBLICATIONS

Loukeris et al. "Introduction of the transposable element Minos into the germ line of *Drosophila melangaster*" Proc. Natl. Acad. Sci. USA 92, 9485–9489, Oct. 1995.

Loukeris et al. "Gene transfer into the medfly, *Ceratitis capitata*, with *Drosophila hydei* transposable element" Science 270, 2002–2005, Dec. 1995.

Minos–2 DNA Sequence submitted to EMBL Data Library by Charalambos Savakis; Released by EMBL Data Library on Sep. 12, 1991.

Franz, Gerald and Savakis, Charalambos, "*Minos*, a new transposable element from *Drosophila hydei*, is a member of the Tc1–like family of transposons," *Nucl. Acids Res.* 19(23):6646 (1991).

Franz, Gerald et al., "Mobile Minos elements from *Drosophila hydei* encode a two–exon transposase with similarity to the paired DNA–binding domain," *Proc. Natl. Acad. Sci. USA* 91(11): 4746–4750 (1994).

*Primary Examiner*—Rebecca E. Prouty
*Assistant Examiner*—Nashaat T. Nashed
*Attorney, Agent, or Firm*—Hamilton, Brook, Smith & Reynolds, P.C.

[57] ABSTRACT

Disclosed are isolated transposable elements, or isolated DNA sequences which encode a transposase protein (or a portion of a transposase protein). The isolated transposable elements or the isolated DNA sequences being characterized by the ability to hybridize to the DNA sequence of Minos-1. The invention also relates to a purified transposase protein, or peptide fragments thereof, encoded by such DNA sequences. Such transposable are useful in methods for the stable introduction of a DNA sequence of interest into a cell. The invention further relates to transgenic animals produced by such methods. The sequence information disclosed herein is useful in the design of oligonucleotide primers which are useful for the isolation of related members of the Tc-1 family of transposable elements.

5 Claims, 8 Drawing Sheets

```
acgagcccaaccactattaattcgaacagcatgttttttgcagtgcgcaatgttta       60
cacactatattatcaatactaaagataacacatccaatgcattcgtctcaaagag        120
aattttattctcttcacgacgaaaaaagtttgctctattccaacaacaacaaaaa        180
tatgagtaatttattcaaacgtttgcttaagagataagaaaagtgaccactattaat     240
tcgaacgcggcgtaaGCTTACCTTAATCTCAAGAGAGCAAAACAAAAGCAACTAATGTA   300
                 M  S  Q  Y  S  M  Q  K  N
ACGGAATCATTATCTAGTTATGATCTGCAAATAATGTCACAATACAGCATGCAAAAAAAT  360
 F  R  L  L  Q  I  S  R  S  L  A  T  M  V  R  G  K  P  I  S    8
TTTAGATTGCTGCAGATCAGTAGAAGTTTAGCAACGATGGTTCGTGGTAAACCTATTTCT  420
 K  E  I  R  V  L  I  R  D  Y  F  K  S  G  K  T  L  T  E  I   28
AAAGAAATCAGAGTATTGATTAGGGATTATTTTAAATCTGGAAAGACACTTACGGAGATA  480
 S  K  Q  L  N  L  P  K  S  S  V  H  G  V  I  Q  I  F  K  K   48
AGCAAGCAATTAAATTTGCCTAAGTCGTCTGTGCATGGGGTGATACAAATTTTCAAAAAA  540
 N  G  N  I  E  N  N  I  A  N  R  G  R  T  S  A  I  T  P  R   68
AATGGGAATATTGAAAATAACATTGCGAATAGAGGCCGAACATCAGCAATAACACCCCGC  600
 D  K  R  Q  L  A  K  I  V  K  A  D  R  R  Q  S  L  R  N  L   88
GACAAAAGACAACTGGCCAAAATTGTTAAGGCTGATCGTCGCCAATCTTTGAGAAATTTG  660
 A  S  K  W  S  Q  Q  L  A  K  L  S  S  E  S  G  R  D  K  L  108
GCTTCTAAGTGGTCGCAGCAATTGGCAAAACTGTCAAGCGAGAGTGGACGCGACAAATTA  720
 K  S  I  G  Y  G  F  Y  K                                    118
AAAAGTATTGGATATGGTTTTTATAAgtatgttttgttattacctgtgcatcgtaccca   780
                  A  K  E  K  P  L  L  T  L  R              128
ataacttactactcgtaatcttactcgtagGCCAAGGAAAAACCCTTGCTTACGCTTCAA  840
```

FIGURE 1A

```
                                                              *
K   K   K   R   L   Q   W   A   R   E   R   M   S   W   T   Q   R   Q   W   D      148
AAAAAGAAGCGTTTGCAATGGGCTCGGGGAAAGGATGTCTTGGACTCAAAGGCAATGGGAT                       900
                                                             A

T   I   I   F   S   D   E   A   K   F   D   V   S   V   G   D   T   R   K   R      168
ACCATCATATTCAGCGATGAAGCTAAATTTGATGTTAGTGTCGGCGATACGAGAAAACGC                       960

V   I   R   K   R   S   E   T   Y   H   K   D   C   L   K   R   T   T   K   F      188
GTCATCCGTAAGAGAGTTCAGAAACATACCATAAAGACTGCCTTAAAAGAACAACAAAGTTT                     1020

P   A   S   T   M   V   W   G   C   M   S   A   K   G   L   G   K   L   H   F      208
CCTGCGAGCACTATGGTATGGGGATGTATGTCTGCCAAAGGATTAGGAAAACTTCATTTC                       1080

I   E   G   T   V   N   A   E   K   Y   I   N   I   L   Q   D   S   L   L   P      228
ATTGAAGGGACAGTTAATGCTGAAAAATATATTAATATTTTACAAGATAGTTTGTTGCCA                       1140

L
S   I   P   K   L   S   D   C   G   E   F   F   Q   Q   D   G   A   S   S          248
TCAATACCAAAACTATCAGATTGCGGTGAATTCACTTTTCAGCAGGACGGAGCATCATCG                       1200
            T

H   T   A   K   R   T   K   N   W   L   Q   Y   N   Q   M   E   V   L   D   W      268
CACACAGCCAAGCGAACCAAAAATTGGCTGCAATATAATCAAATGGAGGTTTTAGATTGG                       1260

P   S   N   S   P   D   L   S   P   I   E   N   I   W   L   M   K   N   Q          288
CCATCAAATAGTCCAGATCTAAGCCCAATTGAAAATATTTGGTGGCTAATGAAAAACCAG                       1320

L   R   N   E   P   Q   R   N   I   S   D   L   K   I   K   L   Q   E   M   W      308
CTTCGAAATGAGCCACAAAGGAATATTTCTGACTTGAAAATCAAGTTGCAAGAGATGTGG                       1380

D   S   I   S   Q   E   H   C   K   N   L   L   S   S   M   P   K   R   V   K      328
GACTCAATTTCTCAAGAGCATTGCAAAAATTTGTTAAGCTCAATGCCAAAACGAGTTAAA                       1440

C   V   M   Q   A   K   G   D   V   T   Q   F                                      341
TGCGTAATGCAGGCCAAGGGCGACGTTACACAATTCTAATATTAATTAAATTATTGTTTT                       1500
```

FIGURE 1B

```
AAGTATGATAGTAAATCACAttacgcccgcgttcgaattaatagtggtcacttttttctta  1560
tctcttaagcaaaccgtttgaataaattactcatatttttgttgttgttggaaatagagc   1620
aaaacttttttttcgtcgtgaagagaataaaattctctttgagacgaaatgcattggta    1680
tgtgttatctttagtagtattgataatatagtgtgttaaacattgcgcactgcaaaaaaa   1740
acatgctgttcgaattaatagtggttggggctcgt   1775
```

FIGURE 1C

```
acgagcccaccactattaattcgaacagcatgttttttgcagtgcgcaatgtttaa              60
cacactatattcaatactaaagataacacataccaatgcattcgtctcaaagag               120
aattttattctcttcacgacgaaaaaaagtttgctctattccaacaacaacaaaaa             180
tatgagtaatttattcaaacgtttgcttaagagataagaaaaagtgaccactattaat           240
tcgaacgcggcgtaaGCTTACCTTAATCTCAAGAGCAAAACAAAAGCAACTAATGTA            300
ACGGAATCATTATCTAGTTATGATCTGCAAATAATGTCACATACAGCATGCAAAAAAAT          360
                M   V   R   G   K   P   I   S                          8
TTTAGAATTGCTGCAGATCAGTAGAAGTTTAGCAACGATGGTTCGTGGTAAACCTATTTC         420
 K   E   I   R   V   L   I   R   D   Y   F   K   S   G   K   T   L   T   E   I     28
TAAAGAAATCAGAGTATTGATTAGGGATTATTTTAAATCTGGAAAGACACTTACGGAGAT         480
 S   K   Q   L   N   L   P   K   S   S   V   H   G   V   I   Q   F   K   K         48
AAGCAAGCAATTAAATTGCCTAAGTCGTCTGTGCATGGGGTGATACAAATTTTCAAAAA          540
 N   G   N   I   E   N   N   I   A   N   R   G   R   T   S   A   I   T   P   R     68
AAATGGGAATATTGAAAATAACATTGCGAATAGAGGCCGAACATCAGCAATAACACCCCG         600
 D   K   R   Q   L   A   K   I   V   K   A   D   R   R   Q   S   L   R   N   L     88
CGACAAAAGACAACTGGCCAAAATTGTTAAGGCTGATCGTCGCCAATCTTTGAGAAATTT         660
 A   S   K   W   S   Q   T   I   G   K   T   V   K   R   E   W   T   R   Q   Q    108
GGCTTCTAAGTGGTCGCAGACAATTGGCAAAACTGTCAAGCGAGAGTGGACGCGACAGCA         720
 L   K   S   I   G   Y   G   F   Y   K                                            118
ATTAAAAAGTATTGGATATGGTTTTTATAAAgtatgttttgttattacctgtgcatcgta         780
                              A   K   E   K   P   L   L   T   L   R            128
cccaataacttactgtaatcttactcgtagGCCAAGGAAAAACCCTTGCTTACGCTTCG          840
```

FIGURE 2A

```
Q   K   K   K   R   L   Q   W   A   R   E   R   M   S   W   T   Q   R   Q   W              148
                                                                        *                    900
                                                                        A
TCAAAAAAGAAGCGTTTGCAATGGGCTCGGGAAAGGATGTCTTGGACTCAAAGGCAATG

D   T   I   I   F   S   D   E   A   K   F   D   V   S   V   G   D   T   R   K              168
                                                                                             960
GGATACCATCATATTCAGCGATGAAGCTAAATTTGATGTTAGTGTCGGCGATACGAGAAA

R   V   I   R   K   R   S   E   T   Y   H   K   D   C   L   K   R   T   T   K              188
                                                                                            1020
ACGCGTCATCCGTAAGAGGTCAGAAACATACCATAAAGACTGCCTAAAAGAACAACAAA

F   P   A   S   T   M   V   W   G   C   M   S   A   K   G   L   G   K   L   H              208
                                                                                            1080
GTTCCTGCGAGCACTATGGTATGGGGATGTATGTCTGCCAAAGGATTAGGAAAACTTCA

F   I   E   G   T   V   N   A   E   K   Y   I   N   I   L   Q   D   S   L   L              228
                                                                                            1140
TTTCATTGAAGGGACAGTTAATGCTGAAAAATATATTAATATTTTACAAGATAGTTTGTT

L
P   S   I   P   K   L   S   D   C   G   E   F   T   F   Q   Q   D   G   A   S              248
    T                                                                                       1200
GCCATCAATACCAAAACTATCAGATTGCGGTGAATTCACTTTTCAGCAGGACGGAGCATC

S   H   T   A   K   R   T   K   N   W   L   Q   Y   N   Q   M   E   V   L   D              268
                                                                                            1260
ATCGCACACAGCCAAGCGAACCAAAAATTGGCTGCAATATAATCAAATGGAGGTTTTAGA

W   P   S   N   S   P   D   L   S   P   I   E   N   I   W   L   M   K   N                  288
                                                                                            1320
TTGGCCATCAAATAGTCCAGATCTAAGCCCAATTGAAAATATTTGGTTGGCTAATGAAAAA

Q   L   R   N   E   P   Q   R   N   I   S   D   L   K   I   K   L   Q   E   M              308
                                                                                            1380
CCAGCTTCGAAATGAGCCACAAAGGAATATTTCTGACTTGAAAATCAAGTTGCAAGAGAT

W   D   S   I   S   Q   E   H   C   K   N   L   L   S   S   M   P   K   R   V              328
                                                                                            1440
GTGGGACTCAATTTCTCAAGAGCATTGCAAAAATTTGTTAAGCTCAATGCCAAAACGAGT

K   C   V   M   Q   A   K   G   D   V   T   Q   F                                           341
                                                                                            1500
TAAATGCGTAATGCAGGCCAAGGGCGACGTTACACACAATTCTAATATTAATTAAATTATTG

FIGURE 2B
```

TTTTAAGTATGATAGTAAATCACAttacgcccgcgttcgaattaatagtggtcactttt 1560
cttatctcttaagcaaaccgtttgaataaattactcatattttgttgttgttggaaata 1620
gagcaaactttttttcgtcgtgaagagaataaaattctctttgagacgaaatgcatt 1680
ggtatgtgttatctttagtagtattgataatatagtgtgttaaacattgcgcactgcaaa 1740
aaaaacatgctgttcgaattaatagtggttggggctcgt 1779

FIGURE 2C

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 1775 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
ACGAGCCCCA  ACCACTATTA  ATTCGAACAG  CATGTTTTTT  TTGCAGTGCG  CAATGTTTAA      60

CACACTATAT  TATCAATACT  ACTAAAGATA  ACACATACCA  ATGCATTTCG  TCTCAAAGAG     120

AATTTTATTC  TCTTCACGAC  GAAAAAAAAA  GTTTTGCTCT  ATTTCCAACA  ACAACAAAAA     180

TATGAGTAAT  TTATTCAAAC  GGTTTGCTTA  AGAGATAAGA  AAAAGTGAC   CACTATTAAT     240

TCGAACGCGG  CGTAAGCTTA  CCTTAATCTC  AAGAAGAGCA  AAACAAAAGC  AACTAATGTA     300

ACGGAATCAT  TATCTAGTTA  TGATCTGCAA  ATAATGTCAC  AATACAGCAT  GCAAAAAAAT     360

TTTAGATTGC  TGCAGATCAG  TAGAAGTTTA  GCAACGATGG  TTCGTGGTAA  ACCTATTTCT     420

AAAGAAATCA  GAGTATTGAT  TAGGGATTAT  TTTAAATCTG  GAAAGACACT  TACGGAGATA     480

AGCAAGCAAT  TAAATTTGCC  TAAGTCGTCT  GTGCATGGGG  TGATACAAAT  TTTCAAAAAA     540
```

| | | | | | |
|---|---|---|---|---|---|
| AATGGGAATA | TTGAAAATAA | CATTGCGAAT | AGAGGCCGAA | CATCAGCAAT | AACACCCCGC | 600 |
| GACAAAAGAC | AACTGGCCAA | AATTGTTAAG | GCTGATCGTC | GCCAATCTTT | GAGAAATTTG | 660 |
| GCTTCTAAGT | GGTCGCAGCA | ATTGGCAAAA | CTGTCAAGCG | AGAGTGGACG | CGACAAATTA | 720 |
| AAAAGTATTG | GATATGGTTT | TTATAAAGTA | TGTTTTGTTA | TTACCTGTGC | ATCGTACCCA | 780 |
| ATAACTTACT | CGTAATCTTA | CTCGTAGGCC | AAGGAAAAAC | CCTTGCTTAC | GCTTCGTCAA | 840 |
| AAAAGAAGC | GTTTGCAATG | GGCTCGGGAA | AGGATGTCTT | GGACTCAAAG | GCAATAGGAT | 900 |
| ACCATCATAT | TCAGCGATGA | AGCTAAATTT | GATGTTAGTG | TCGGCGATAC | GAGAAACGC | 960 |
| GTCATCCGTA | AGAGGTCAGA | AACATACCAT | AAAGACTGCC | TTAAAAGAAC | AACAAAGTTT | 1020 |
| CCTGCGAGCA | CTATGGTATG | GGGATGTATG | TCTGCCAAAG | GATTAGGAAA | ACTTCATTTC | 1080 |
| ATTGAAGGGA | CAGTTAATGC | TGAAAAATAT | ATTAATATTT | TACAAGATAG | TTTGTTGCCA | 1140 |
| TCAATACCAA | AACTATCAGA | TTGCGGTGAA | TTCACTTTTC | AGCAGGACGG | AGCATCATCG | 1200 |
| CACACAGCCA | AGCGAACCAA | AAATTGGCTG | CAATATAATC | AAATGGAGGT | TTTAGATTGG | 1260 |
| CCATCAAATA | GTCCAGATCT | AAGCCCAATT | GAAAATATTT | GGTGGCTAAT | GAAAAACCAG | 1320 |
| CTTCGAAATG | AGCCACAAAG | GAATATTTCT | GACTTGAAAA | TCAAGTTGCA | AGAGATGTGG | 1380 |
| GACTCAATTT | CTCAAGAGCA | TTGCAAAAAT | TTGTTAAGCT | CAATGCCAAA | ACGAGTTAAA | 1440 |
| TGCGTAATGC | AGGCCAAGGG | CGACGTTACA | CAATTCTAAT | ATTAATTAAA | TTATTGTTTT | 1500 |
| AAGTATGATA | GTAAATCACA | TTACGCCGCG | TTCGAATTAA | TAGTGGTCAC | TTTTTTCTTA | 1560 |
| TCTCTTAAGC | AAACCGTTTG | AATAAATTAC | TCATATTTTT | GTTGTTGTTG | GAAATAGAGC | 1620 |
| AAAACTTTTT | TTTTCGTCGT | GAAGAGAATA | AAATTCTCTT | TGAGACGAAA | TGCATTGGTA | 1680 |
| TGTGTTATCT | TTAGTAGTAT | TGATAATATA | GTGTGTTAAA | CATTGCGCAC | TGCAAAAAAA | 1740 |
| ACATGCTGTT | CGAATTAATA | GTGGTTGGGG | CTCGT | | | 1775 |

( 2 ) INFORMATION FOR SEQ ID NO:2:

( i ) SEQUENCE CHARACTERISTICS:
        ( A ) LENGTH: 1775 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

| | | | | | |
|---|---|---|---|---|---|
| ACGAGCCCCA | ACCACTATTA | ATTCGAACAG | CATGTTTTTT | TTGCAGTGCG | CAATGTTTAA | 60 |
| CACACTATAT | TATCAATACT | ACTAAAGATA | ACACATACCA | ATGCATTTCG | TCTCAAAGAG | 120 |
| AATTTTATTC | TCTTCACGAC | GAAAAAAAAA | GTTTTGCTCT | ATTTCCAACA | ACAACAAAAA | 180 |
| TATGAGTAAT | TTATTCAAAC | GGTTTGCTTA | AGAGATAAGA | AAAAGTGAC | CACTATTAAT | 240 |
| TCGAACGCGG | CGTAAGCTTA | CCTTAATCTC | AAGAAGAGCA | AACAAAGC | AACTAATGTA | 300 |
| ACGGAATCAT | TATCTAGTTA | TGATCTGCAA | ATAATGTCAC | AATACAGCAT | GCAAAAAAT | 360 |
| TTTAGATTGC | TGCAGATCAG | TAGAAGTTTA | GCAACGATGG | TTCGTGGTAA | ACCTATTTCT | 420 |
| AAAGAAATCA | GAGTATTGAT | TAGGGATTAT | TTTAAATCTG | GAAAGACACT | TACGGAGATA | 480 |
| AGCAAGCAAT | TAAATTTGCC | TAAGTCGTCT | GTGCATGGGG | TGATACAAAT | TTTCAAAAAA | 540 |
| AATGGGAATA | TTGAAAATAA | CATTGCGAAT | AGAGGCCGAA | CATCAGCAAT | AACACCCCGC | 600 |
| GACAAAAGAC | AACTGGCCAA | AATTGTTAAG | GCTGATCGTC | GCCAATCTTT | GAGAAATTTG | 660 |
| GCTTCTAAGT | GGTCGCAGCA | ATTGGCAAAA | CTGTCAAGCG | AGAGTGGACG | CGACAAATTA | 720 |
| AAAAGTATTG | GATATGGTTT | TTATAAAGTA | TGTTTTGTTA | TTACCTGTGC | ATCGTACCCA | 780 |

```
ATAACTTACT  CGTAATCTTA  CTCGTAGGCC  AAGGAAAAAC  CCTTGCTTAC  GCTTCGTCAA      840
AAAAAGAAGC  GTTTGCAATG  GGCTCGGGAA  AGGATGTCTT  GGACTCAAAG  GCAATGGGAT      900
ACCATCATAT  TCAGCGATGA  AGCTAAATTT  GATGTTAGTG  TCGGCGATAC  GAGAAAACGC      960
GTCATCCGTA  AGAGGTCAGA  AACATACCAT  AAAGACTGCC  TTAAAAGAAC  AACAAAGTTT     1020
CCTGCGAGCA  CTATGGTATG  GGGATGTATG  TCTGCCAAAG  GATTAGGAAA  ACTTCATTTC     1080
ATTGAAGGGA  CAGTTAATGC  TGAAAAATAT  ATTAATATTT  TACAAGATAG  TTTGTTGCCA     1140
TCAATACCAA  AACTATTAGA  TTGCGGTGAA  TTCACTTTTC  AGCAGGACGG  AGCATCATCG     1200
CACACAGCCA  AGCGAACCAA  AAATTGGCTG  CAATATAATC  AAATGGAGGT  TTTAGATTGG     1260
CCATCAAATA  GTCCAGATCT  AAGCCCAATT  GAAATATTT   GGTGGCTAAT  GAAAACCAG      1320
CTTCGAAATG  AGCCACAAAG  GAATATTTCT  GACTTGAAAA  TCAAGTTGCA  AGAGATGTGG     1380
GACTCAATTT  CTCAAGAGCA  TTGCAAAAAT  TTGTTAAGCT  CAATGCCAAA  ACGAGTTAAA     1440
TGCGTAATGC  AGGCCAAGGG  CGACGTTACA  CAATTCTAAT  ATTAATTAAA  TTATTGTTTT     1500
AAGTATGATA  GTAAATCACA  TTACGCCGCG  TTCGAATTAA  TAGTGGTCAC  TTTTTTCTTA     1560
TCTCTTAAGC  AAACCGTTTG  AATAAATTAC  TCATATTTTT  GTTGTTGTTG  GAAATAGAGC     1620
AAAACTTTTT  TTTTCGTCGT  GAAGAGAATA  AAATTCTCTT  TGAGACGAAA  TGCATTGGTA     1680
TGTGTTATCT  TTAGTAGTAT  TGATAATATA  GTGTGTTAAA  CATTGCGCAC  TGCAAAAAAA     1740
ACATGCTGTT  CGAATTAATA  GTGGTTGGGG  CTCGT                                  1775
```

(2) INFORMATION FOR SEQ ID NO:3:

(i) SEQUENCE CHARACTERISTICS:
        (A) LENGTH: 1775 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

```
ACGAGCCCCA  ACCACTATTA  ATTCGAACAG  CATGTTTTTT  TTGCAGTGCG  CAATGTTTAA       60
CACACTATAT  TATCAATACT  ACTAAAGATA  ACACATACCA  ATGCATTTCG  TCTCAAAGAG      120
AATTTTATTC  TCTTCACGAC  GAAAAAAAAA  GTTTTGCTCT  ATTCCAACA   ACAACAAAAA      180
TATGAGTAAT  TTATTCAAAC  GGTTTGCTTA  AGAGATAAGA  AAAAAGTGAC  CACTATTAAT      240
TCGAACGCGG  CGTAAGCTTA  CCTTAATCTC  AAGAAGAGCA  AAACAAAAGC  AACTAATGTA      300
ACGGAATCAT  TATCTAGTTA  TGATCTGCAA  ATAATGTCAC  AATACAGCAT  GCAAAAAAAT      360
TTTAGATTGC  TGCAGATCAG  TAGAAGTTTA  GCAACGATGG  TTCGTGGTAA  ACCTATTTCT      420
AAAGAAATCA  GAGTATTGAT  TAGGGATTAT  TTTAAATCTG  GAAAGACACT  TACGGAGATA      480
AGCAAGCAAT  TAAATTTGCC  TAAGTCGTCT  GTGCATGGGG  TGATACAAAT  TTTCAAAAAA      540
AATGGGAATA  TTGAAAATAA  CATTGCGAAT  AGAGGCCGAA  CATCAGCAAT  AACACCCCGC      600
GACAAAAGAC  AACTGGCCAA  AATTGTTAAG  GCTGATCGTC  GCCAATCTTT  GAGAAATTTG      660
GCTTCTAAGT  GGTCGCAGCA  ATTGGCAAAA  CTGTCAAGCG  AGAGTGGACG  CGACAAATTA      720
AAAAGTATTG  GATATGGTTT  TTATAAAGTA  TGTTTTGTTA  TTACCTGTGC  ATCGTACCCA      780
ATAACTTACT  CGTAATCTTA  CTCGTAGGCC  AAGGAAAAAC  CCTTGCTTAC  GCTTCGTCAA      840
AAAAAGAAGC  GTTTGCAATG  GGCTCGGGAA  AGGATGTCTT  GGACTCAAAG  GCAATGGGAT      900
ACCATCATAT  TCAGCGATGA  AGCTAAATTT  GATGTTAGTG  TCGGCGATAC  GAGAAAACGC      960
```

| | | | | | |
|---|---|---|---|---|---|
| GTCATCCGTA | AGAGGTCAGA | AACATACCAT | AAAGACTGCC | TTAAAAGAAC | AACAAAGTTT | 1020
| CCTGCGAGCA | CTATGGTATG | GGGATGTATG | TCTGCCAAAG | GATTAGGAAA | ACTTCATTTC | 1080
| ATTGAAGGGA | CAGTTAATGC | TGAAAAATAT | ATTAATATTT | TACAAGATAG | TTTGTTGCCA | 1140
| TCAATACCAA | AACTATCAGA | TTGCGGTGAA | TTCACTTTTC | AGCAGGACGG | AGCATCATCG | 1200
| CACACAGCCA | AGCGAACCAA | AAATTGGCTG | CAATATAATC | AAATGGAGGT | TTTAGATTGG | 1260
| CCATCAAATA | GTCCAGATCT | AAGCCCAATT | GAAAATATTT | GGTGGCTAAT | GAAAAACCAG | 1320
| CTTCGAAATG | AGCCACAAAG | GAATATTTCT | GACTTGAAAA | TCAAGTTGCA | AGAGATGTGG | 1380
| GACTCAATTT | CTCAAGAGCA | TTGCAAAAAT | TTGTTAAGCT | CAATGCCAAA | ACGAGTTAAA | 1440
| TGCGTAATGC | AGGCCAAGGG | CGACGTTACA | CAATTCTAAT | ATTAATTAAA | TTATTGTTTT | 1500
| AAGTATGATA | GTAAATCACA | TTACGCCGCG | TTCGAATTAA | TAGTGGTCAC | TTTTTTCTTA | 1560
| TCTCTTAAGC | AAACCGTTTG | AATAAATTAC | TCATATTTTT | GTTGTTGTTG | GAAATAGAGC | 1620
| AAAACTTTTT | TTTTCGTCGT | GAAGAGAATA | AAATTCTCTT | TGAGACGAAA | TGCATTGGTA | 1680
| TGTGTTATCT | TTAGTAGTAT | TGATAATATA | GTGTGTTAAA | CATTGCGCAC | TGCAAAAAAA | 1740
| ACATGCTGTT | CGAATTAATA | GTGGTTGGGG | CTCGT | | | 1775

( 2 ) INFORMATION FOR SEQ ID NO:4:

( i ) SEQUENCE CHARACTERISTICS:
        ( A ) LENGTH: 1779 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: join(398..751, 812..898)

( x i ) SEQUENCE DESCRIPTION: SEQ ID NO:4:

```
ACGAGCCCCA ACCACTATTA ATTCGAACAG CATGTTTTTT TTGCAGTGCG CAATGTTTAA      60

CACACTATAT TATCAATACT ACTAAAGATA ACACATACCA ATGCATTTCG TCTCAAAGAG     120

AATTTTATTC TCTTCACGAC GAAAAAAAAA GTTTTGCTCT ATTTCCAACA ACAACAAAAA     180

TATGAGTAAT TTATTCAAAC GGTTTGCTTA AGAGATAAGA AAAAGTGAC CACTATTAAT      240

TCGAACGCGG CGTAAGCTTA CCTTAATCTC AAGAAGAGCA AACAAAAGC AACTAATGTA      300

ACGGAATCAT TATCTAGTTA TGATCTGCAA ATAATGTCAC AATACAGCAT GCAAAAAAAT     360

TTTAGAATTG CTGCAGATCA GTAGAAGTTT AGCAACG ATG GTT CGT GGT AAA CCT     415
                                          Met Val Arg Gly Lys Pro
                                            1               5
```

```
ATT TCT AAA GAA ATC AGA GTA TTG ATT AGG GAT TAT TTT AAA TCT GGA      463
Ile Ser Lys Glu Ile Arg Val Leu Ile Arg Asp Tyr Phe Lys Ser Gly
         10              15              20

AAG ACA CTT ACG GAG ATA AGC AAG CAA TTA AAT TTG CCT AAG TCG TCT      511
Lys Thr Leu Thr Glu Ile Ser Lys Gln Leu Asn Leu Pro Lys Ser Ser
     25              30              35

GTG CAT GGG GTG ATA CAA ATT TTC AAA AAA AAT GGG AAT ATT GAA AAT      559
Val His Gly Val Ile Gln Ile Phe Lys Lys Asn Gly Asn Ile Glu Asn
     40              45              50

AAC ATT GCG AAT AGA GGC CGA ACA TCA GCA ATA ACA CCC CGC GAC AAA      607
Asn Ile Ala Asn Arg Gly Arg Thr Ser Ala Ile Thr Pro Arg Asp Lys
 55              60              65              70

AGA CAA CTG GCC AAA ATT GTT AAG GCT GAT CGT CGC CAA TCT TTG AGA      655
Arg Gln Leu Ala Lys Ile Val Lys Ala Asp Arg Arg Gln Ser Leu Arg
             75              80              85
```

```
AAT TTG GCT TCT AAG TGG TCG CAG ACA ATT GGC AAA ACT GTC AAG CGA        703
Asn Leu Ala Ser Lys Trp Ser Gln Thr Ile Gly Lys Thr Val Lys Arg
             90                  95                 100

GAG TGG ACG CGA CAG CAA TTA AAA AGT ATT GGA TAT GGT TTT TAT AAA        751
Glu Trp Thr Arg Gln Gln Leu Lys Ser Ile Gly Tyr Gly Phe Tyr Lys
            105                 110                 115

GTATGTTTTG TTATTACCTG TGCATCGTAC CCAATAACTT ACTCGTAATC TTACTCGTAG      811

GCC AAG GAA AAA CCC TTG CTT ACG CTT CGT CAA AAA AAG AAG CGT TTG        859
Ala Lys Glu Lys Pro Leu Leu Thr Leu Arg Gln Lys Lys Lys Arg Leu
        120             125                 130

CAA TGG GCT CGG GAA AGG ATG TCT TGG ACT CAA AGG CAA TAGGATACCA         908
Gln Trp Ala Arg Glu Arg Met Ser Trp Thr Gln Arg Gln
135             140                 145

TCATATTCAG CGATGAAGCT AAATTTGATG TTAGTGTCGG CGATACGAGA AAACGCGTCA      968
TCCGTAAGAG GTCAGAAACA TACCATAAAG ACTGCCTTAA AAGAACAACA AAGTTTCCTG     1028
CGAGCACTAT GGTATGGGGA TGTATGTCTG CCAAAGGATT AGGAAAACTT CATTTCATTG     1088
AAGGGACAGT TAATGCTGAA AAATATATTA ATATTTTACA AGATAGTTTG TTGCCATCAA     1148
TACCAAAACT ATCAGATTGC GGTGAATTCA CTTTTCAGCA GGACGGAGCA TCATCGCACA     1208
CAGCCAAGCG AACCAAAAAT TGGCTGCAAT ATAATCAAAT GGAGGTTTTA GATTGGCCAT     1268
CAAATAGTCC AGATCTAAGC CCAATTGAAA ATATTTGGTG GCTAATGAAA AACCAGCTTC     1328
GAAATGAGCC ACAAAGGAAT ATTTCTGACT TGAAAATCAA GTTGCAAGAG ATGTGGGACT     1388
CAATTTCTCA AGAGCATTGC AAAAATTTGT TAAGCTCAAT GCCAAAACGA GTTAAATGCG     1448
TAATGCAGGC CAAGGGCGAC GTTACACAAT TCTAATATTA ATTAAATTAT TGTTTTAAGT     1508
ATGATAGTAA ATCACATTAC GCCGCGTTCG AATTAATAGT GGTCACTTTT TTCTTATCTC     1568
TTAAGCAAAC CGTTTGAATA AATTACTCAT ATTTTTGTTG TTGTTGGAAA TAGAGCAAAA     1628
CTTTTTTTTT CGTCGTGAAG AGAATAAAAT TCTCTTTGAG ACGAAATGCA TTGGTATGTG     1688
TTATCTTTAG TAGTATTGAT AATATAGTGT GTTAAACATT GCGCACTGCA AAAAAAACAT    1748
GCTGTTCGAA TTAATAGTGG TTGGGGCTCG T                                    1779
```

( 2 ) INFORMATION FOR SEQ ID NO:5:

( i ) SEQUENCE CHARACTERISTICS:
      ( A ) LENGTH: 147 amino acids
      ( B ) TYPE: amino acid
      ( D ) TOPOLOGY: linear ( i i ) MOLECULE TYPE: protein ( x i ) SEQUENCE DESCRIPTION: SEQ ID NO:5:

```
Met Val Arg Gly Lys Pro Ile Ser Lys Glu Ile Arg Val Leu Ile Arg
 1               5                  10                  15

Asp Tyr Phe Lys Ser Gly Lys Thr Leu Thr Glu Ile Ser Lys Gln Leu
                20                  25                  30

Asn Leu Pro Lys Ser Ser Val His Gly Val Ile Gln Ile Phe Lys Lys
            35                  40                  45

Asn Gly Asn Ile Glu Asn Asn Ile Ala Asn Arg Gly Arg Thr Ser Ala
        50                  55                  60

Ile Thr Pro Arg Asp Lys Arg Gln Leu Ala Lys Ile Val Lys Ala Asp
65                  70                  75                  80

Arg Arg Gln Ser Leu Arg Asn Leu Ala Ser Lys Trp Ser Gln Thr Ile
                85                  90                  95

Gly Lys Thr Val Lys Arg Glu Trp Thr Arg Gln Gln Leu Lys Ser Ile
```

|   |   |   | 100 |   |   |   |   | 105 |   |   |   |   | 110 |   |   |
|---|---|---|---|---|---|---|---|---|---|---|---|---|---|---|---|
| Gly | Tyr | Gly | Phe | Tyr | Lys | Ala | Lys | Glu | Lys | Pro | Leu | Leu | Thr | Leu | Arg |
|   |   | 115 |   |   |   | 120 |   |   |   |   | 125 |   |   |   |   |

| Gln | Lys | Lys | Lys | Arg | Leu | Gln | Trp | Ala | Arg | Glu | Arg | Met | Ser | Trp | Thr |
|---|---|---|---|---|---|---|---|---|---|---|---|---|---|---|---|
|   | 130 |   |   |   |   | 135 |   |   |   | 140 |   |   |   |   |   |

Gln Arg Gln
145

( 2 ) INFORMATION FOR SEQ ID NO:6:

( i ) SEQUENCE CHARACTERISTICS:
        ( A ) LENGTH: 1779 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: join(398..751, 812..1480)

( x i ) SEQUENCE DESCRIPTION: SEQ ID NO:6:

```
ACGAGCCCCA ACCACTATTA ATTCGAACAG CATGTTTTTT TTGCAGTGCG CAATGTTTAA      60

CACACTATAT TATCAATACT ACTAAAGATA ACACATACCA ATGCATTTCG TCTCAAAGAG     120

AATTTTATTC TCTTCACGAC GAAAAAAAAA GTTTTGCTCT ATTTCCAACA ACAACAAAAA     180

TATGAGTAAT TTATTCAAAC GGTTTGCTTA AGAGATAAGA AAAAGTGAC CACTATTAAT      240

TCGAACGCGG CGTAAGCTTA CCTTAATCTC AAGAAGAGCA AACAAAAGC AACTAATGTA      300

ACGGAATCAT TATCTAGTTA TGATCTGCAA ATAATGTCAC AATACAGCAT GCAAAAAAT      360

TTTAGAATTG CTGCAGATCA GTAGAAGTTT AGCAACG ATG GTT CGT GGT AAA CCT     415
                                          Met Val Arg Gly Lys Pro
                                           1               5
```

| ATT | TCT | AAA | GAA | ATC | AGA | GTA | TTG | ATT | AGG | GAT | TAT | TTT | AAA | TCT | GGA | 463 |
|---|---|---|---|---|---|---|---|---|---|---|---|---|---|---|---|---|
| Ile | Ser | Lys | Glu | Ile | Arg | Val | Leu | Ile | Arg | Asp | Tyr | Phe | Lys | Ser | Gly |   |
|   |   |   | 10 |   |   |   |   | 15 |   |   |   |   | 20 |   |   |   |

| AAG | ACA | CTT | ACG | GAG | ATA | AGC | AAG | CAA | TTA | AAT | TTG | CCT | AAG | TCG | TCT | 511 |
|---|---|---|---|---|---|---|---|---|---|---|---|---|---|---|---|---|
| Lys | Thr | Leu | Thr | Glu | Ile | Ser | Lys | Gln | Leu | Asn | Leu | Pro | Lys | Ser | Ser |   |
|   |   | 25 |   |   |   |   | 30 |   |   |   |   | 35 |   |   |   |   |

| GTG | CAT | GGG | GTG | ATA | CAA | ATT | TTC | AAA | AAA | AAT | GGG | AAT | ATT | GAA | AAT | 559 |
|---|---|---|---|---|---|---|---|---|---|---|---|---|---|---|---|---|
| Val | His | Gly | Val | Ile | Gln | Ile | Phe | Lys | Lys | Asn | Gly | Asn | Ile | Glu | Asn |   |
|   | 40 |   |   |   |   | 45 |   |   |   |   | 50 |   |   |   |   |   |

| AAC | ATT | GCG | AAT | AGA | GGC | CGA | ACA | TCA | GCA | ATA | ACA | CCC | CGC | GAC | AAA | 607 |
|---|---|---|---|---|---|---|---|---|---|---|---|---|---|---|---|---|
| Asn | Ile | Ala | Asn | Arg | Gly | Arg | Thr | Ser | Ala | Ile | Thr | Pro | Arg | Asp | Lys |   |
| 55 |   |   |   | 60 |   |   |   |   | 65 |   |   |   |   | 70 |   |   |

| AGA | CAA | CTG | GCC | AAA | ATT | GTT | AAG | GCT | GAT | CGT | CGC | CAA | TCT | TTG | AGA | 655 |
|---|---|---|---|---|---|---|---|---|---|---|---|---|---|---|---|---|
| Arg | Gln | Leu | Ala | Lys | Ile | Val | Lys | Ala | Asp | Arg | Arg | Gln | Ser | Leu | Arg |   |
|   |   |   |   | 75 |   |   |   |   | 80 |   |   |   |   | 85 |   |   |

| AAT | TTG | GCT | TCT | AAG | TGG | TCG | CAG | ACA | ATT | GGC | AAA | ACT | GTC | AAG | CGA | 703 |
|---|---|---|---|---|---|---|---|---|---|---|---|---|---|---|---|---|
| Asn | Leu | Ala | Ser | Lys | Trp | Ser | Gln | Thr | Ile | Gly | Lys | Thr | Val | Lys | Arg |   |
|   |   |   | 90 |   |   |   |   | 95 |   |   |   |   | 100 |   |   |   |

| GAG | TGG | ACG | CGA | CAG | CAA | TTA | AAA | AGT | ATT | GGA | TAT | GGT | TTT | TAT | AAA | 751 |
|---|---|---|---|---|---|---|---|---|---|---|---|---|---|---|---|---|
| Glu | Trp | Thr | Arg | Gln | Gln | Leu | Lys | Ser | Ile | Gly | Tyr | Gly | Phe | Tyr | Lys |   |
|   |   | 105 |   |   |   |   | 110 |   |   |   |   | 115 |   |   |   |   |

```
GTATGTTTTG TTATTACCTG TGCATCGTAC CCAATAACTT ACTCGTAATC TTACTCGTAG    811
```

| GCC | AAG | GAA | AAA | CCC | TTG | CTT | ACG | CTT | CGT | CAA | AAA | AAG | AAG | CGT | TTG | 859 |
|---|---|---|---|---|---|---|---|---|---|---|---|---|---|---|---|---|
| Ala | Lys | Glu | Lys | Pro | Leu | Leu | Thr | Leu | Arg | Gln | Lys | Lys | Lys | Arg | Leu |   |
|   | 120 |   |   |   |   | 125 |   |   |   |   | 130 |   |   |   |   |   |

| CAA | TGG | GCT | CGG | GAA | AGG | ATG | TCT | TGG | ACT | CAA | AGG | CAA | TGG | GAT | ACC | 907 |
|---|---|---|---|---|---|---|---|---|---|---|---|---|---|---|---|---|
| Gln | Trp | Ala | Arg | Glu | Arg | Met | Ser | Trp | Thr | Gln | Arg | Gln | Trp | Asp | Thr |   |

```
ATC ATA TTC AGC GAT GAA GCT AAA TTT GAT GTT AGT GTC GGC GAT ACG    955
Ile Ile Phe Ser Asp Glu Ala Lys Phe Asp Val Ser Val Gly Asp Thr
            155             160             165

AGA AAA CGC GTC ATC CGT AAG AGG TCA GAA ACA TAC CAT AAA GAC TGC   1003
Arg Lys Arg Val Ile Arg Lys Arg Ser Glu Thr Tyr His Lys Asp Cys
            170             175             180

CTT AAA AGA ACA ACA AAG TTT CCT GCG AGC ACT ATG GTA TGG GGA TGT   1051
Leu Lys Arg Thr Thr Lys Phe Pro Ala Ser Thr Met Val Trp Gly Cys
            185             190             195

ATG TCT GCC AAA GGA TTA GGA AAA CTT CAT TTC ATT GAA GGG ACA GTT   1099
Met Ser Ala Lys Gly Leu Gly Lys Leu His Phe Ile Glu Gly Thr Val
            200             205             210

AAT GCT GAA AAA TAT ATT AAT ATT TTA CAA GAT AGT TTG TTG CCA TCA   1147
Asn Ala Glu Lys Tyr Ile Asn Ile Leu Gln Asp Ser Leu Leu Pro Ser
215             220             225             230

ATA CCA AAA CTA TTA GAT TGC GGT GAA TTC ACT TTT CAG CAG GAC GGA   1195
Ile Pro Lys Leu Leu Asp Cys Gly Glu Phe Thr Phe Gln Gln Asp Gly
            235             240             245

GCA TCA TCG CAC ACA GCC AAG CGA ACC AAA AAT TGG CTG CAA TAT AAT   1243
Ala Ser Ser His Thr Ala Lys Arg Thr Lys Asn Trp Leu Gln Tyr Asn
            250             255             260

CAA ATG GAG GTT TTA GAT TGG CCA TCA AAT AGT CCA GAT CTA AGC CCA   1291
Gln Met Glu Val Leu Asp Trp Pro Ser Asn Ser Pro Asp Leu Ser Pro
            265             270             275

ATT GAA AAT ATT TGG TGG CTA ATG AAA AAC CAG CTT CGA AAT GAG CCA   1339
Ile Glu Asn Ile Trp Trp Leu Met Lys Asn Gln Leu Arg Asn Glu Pro
            280             285             290

CAA AGG AAT ATT TCT GAC TTG AAA ATC AAG TTG CAA GAG ATG TGG GAC   1387
Gln Arg Asn Ile Ser Asp Leu Lys Ile Lys Leu Gln Glu Met Trp Asp
295             300             305             310

TCA ATT TCT CAA GAG CAT TGC AAA AAT TTG TTA AGC TCA ATG CCA AAA   1435
Ser Ile Ser Gln Glu His Cys Lys Asn Leu Leu Ser Ser Met Pro Lys
            315             320             325

CGA GTT AAA TGC GTA ATG CAG GCC AAG GGC GAC GTT ACA CAA TTC       1480
Arg Val Lys Cys Val Met Gln Ala Lys Gly Asp Val Thr Gln Phe
            330             335             340

TAATATTAAT TAAATTATTG TTTTAAGTAT GATAGTAAAT CACATTACGC CGCGTTCGAA   1540

TTAATAGTGG TCACTTTTTT CTTATCTCTT AAGCAAACCG TTTGAATAAA TTACTCATAT   1600

TTTTGTTGTT GTTGGAAATA GAGCAAAACT TTTTTTTTCG TCGTGAAGAG AATAAAATTC   1660

TCTTTGAGAC GAAATGCATT GGTATGTGTT ATCTTTAGTA GTATTGATAA TATAGTGTGT   1720

TAAACATTGC GCACTGCAAA AAAAACATGC TGTTCGAATT AATAGTGGTT GGGGCTCGT    1779
```

( 2 ) INFORMATION FOR SEQ ID NO:7:

( i ) SEQUENCE CHARACTERISTICS:
        ( A ) LENGTH: 341 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met Val Arg Gly Lys Pro Ile Ser Lys Glu Ile Arg Val Leu Ile Arg
1               5                   10                  15

Asp Tyr Phe Lys Ser Gly Lys Thr Leu Thr Glu Ile Ser Lys Gln Leu
                20                  25                  30

Asn Leu Pro Lys Ser Ser Val His Gly Val Ile Gln Ile Phe Lys Lys
                35                  40                  45
```

```
Asn  Gly  Asn  Ile  Glu  Asn  Asn  Ile  Ala  Asn  Arg  Gly  Arg  Thr  Ser  Ala
     50                 55                      60

Ile  Thr  Pro  Arg  Asp  Lys  Arg  Gln  Leu  Ala  Lys  Ile  Val  Lys  Ala  Asp
65                      70                      75                           80

Arg  Arg  Gln  Ser  Leu  Arg  Asn  Leu  Ala  Ser  Lys  Trp  Ser  Gln  Thr  Ile
               85                      90                           95

Gly  Lys  Thr  Val  Lys  Arg  Glu  Trp  Thr  Arg  Gln  Leu  Lys  Ser  Ile
               100                 105                      110

Gly  Tyr  Gly  Phe  Tyr  Lys  Ala  Lys  Glu  Lys  Pro  Leu  Leu  Thr  Leu  Arg
          115                      120                      125

Gln  Lys  Lys  Arg  Leu  Gln  Trp  Ala  Arg  Glu  Arg  Met  Ser  Trp  Thr
     130                 135                 140

Gln  Arg  Gln  Trp  Asp  Thr  Ile  Ile  Phe  Ser  Asp  Glu  Ala  Lys  Phe  Asp
145                      150                      155                          160

Val  Ser  Val  Gly  Asp  Thr  Arg  Lys  Arg  Val  Ile  Arg  Lys  Arg  Ser  Glu
               165                      170                      175

Thr  Tyr  His  Lys  Asp  Cys  Leu  Lys  Arg  Thr  Thr  Lys  Phe  Pro  Ala  Ser
               180                      185                      190

Thr  Met  Val  Trp  Gly  Cys  Met  Ser  Ala  Lys  Gly  Leu  Gly  Lys  Leu  His
               195                 200                      205

Phe  Ile  Glu  Gly  Thr  Val  Asn  Ala  Glu  Lys  Tyr  Ile  Asn  Ile  Leu  Gln
     210                      215                      220

Asp  Ser  Leu  Leu  Pro  Ser  Ile  Pro  Lys  Leu  Leu  Asp  Cys  Gly  Glu  Phe
225                      230                      235                          240

Thr  Phe  Gln  Gln  Asp  Gly  Ala  Ser  Ser  His  Thr  Ala  Lys  Arg  Thr  Lys
               245                      250                      255

Asn  Trp  Leu  Gln  Tyr  Asn  Gln  Met  Glu  Val  Leu  Asp  Trp  Pro  Ser  Asn
               260                      265                      270

Ser  Pro  Asp  Leu  Ser  Pro  Ile  Glu  Asn  Ile  Trp  Trp  Leu  Met  Lys  Asn
          275                      280                      285

Gln  Leu  Arg  Asn  Glu  Pro  Gln  Arg  Asn  Ile  Ser  Asp  Leu  Lys  Ile  Lys
          290                      295                      300

Leu  Gln  Glu  Met  Trp  Asp  Ser  Ile  Ser  Gln  Glu  His  Cys  Lys  Asn  Leu
305                      310                      315                          320

Leu  Ser  Ser  Met  Pro  Lys  Arg  Val  Lys  Cys  Val  Met  Gln  Ala  Lys  Gly
               325                      330                      335

Asp  Val  Thr  Gln  Phe
               340
```

( 2 ) INFORMATION FOR SEQ ID NO:8:

( i ) SEQUENCE CHARACTERISTICS:
        ( A ) LENGTH: 1779 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: join(398..751, 812..1480)

( x i ) SEQUENCE DESCRIPTION: SEQ ID NO:8:

```
ACGAGCCCCA  ACCACTATTA  ATTCGAACAG  CATGTTTTTT  TTGCAGTGCG  CAATGTTTAA      60

CACACTATAT  TATCAATACT  ACTAAAGATA  ACACATACCA  ATGCATTTCG  TCTCAAAGAG     120

AATTTTATTC  TCTTCACGAC  GAAAAAAAAA  GTTTTGCTCT  ATTTCCAACA  ACAACAAAAA     180
```

```
TATGAGTAAT TTATTCAAAC GGTTTGCTTA AGAGATAAGA AAAAAGTGAC CACTATTAAT      240

TCGAACGCGG CGTAAGCTTA CCTTAATCTC AAGAAGAGCA AAACAAAAGC AACTAATGTA      300

ACGGAATCAT TATCTAGTTA TGATCTGCAA ATAATGTCAC AATACAGCAT GCAAAAAAT       360

TTTAGAATTG CTGCAGATCA GTAGAAGTTT AGCAACG ATG GTT CGT GGT AAA CCT       415
                                          Met Val Arg Gly Lys Pro
                                           1               5
```

| ATT | TCT | AAA | GAA | ATC | AGA | GTA | TTG | ATT | AGG | GAT | TAT | TTT | AAA | TCT | GGA | 463 |
|-----|-----|-----|-----|-----|-----|-----|-----|-----|-----|-----|-----|-----|-----|-----|-----|-----|
| Ile | Ser | Lys | Glu | Ile | Arg | Val | Leu | Ile | Arg | Asp | Tyr | Phe | Lys | Ser | Gly | |
| | | | 10 | | | | | 15 | | | | | 20 | | | |

| AAG | ACA | CTT | ACG | GAG | ATA | AGC | AAG | CAA | TTA | AAT | TTG | CCT | AAG | TCG | TCT | 511 |
|-----|-----|-----|-----|-----|-----|-----|-----|-----|-----|-----|-----|-----|-----|-----|-----|-----|
| Lys | Thr | Leu | Thr | Glu | Ile | Ser | Lys | Gln | Leu | Asn | Leu | Pro | Lys | Ser | Ser | |
| | | | 25 | | | | | 30 | | | | | 35 | | | |

| GTG | CAT | GGG | GTG | ATA | CAA | ATT | TTC | AAA | AAA | AAT | GGG | AAT | ATT | GAA | AAT | 559 |
|-----|-----|-----|-----|-----|-----|-----|-----|-----|-----|-----|-----|-----|-----|-----|-----|-----|
| Val | His | Gly | Val | Ile | Gln | Ile | Phe | Lys | Lys | Asn | Gly | Asn | Ile | Glu | Asn | |
| | | 40 | | | | | 45 | | | | | 50 | | | | |

| AAC | ATT | GCG | AAT | AGA | GGC | CGA | ACA | TCA | GCA | ATA | ACA | CCC | CGC | GAC | AAA | 607 |
|-----|-----|-----|-----|-----|-----|-----|-----|-----|-----|-----|-----|-----|-----|-----|-----|-----|
| Asn | Ile | Ala | Asn | Arg | Gly | Arg | Thr | Ser | Ala | Ile | Thr | Pro | Arg | Asp | Lys | |
| 55 | | | | | 60 | | | | | 65 | | | | | 70 | |

| AGA | CAA | CTG | GCC | AAA | ATT | GTT | AAG | GCT | GAT | CGT | CGC | CAA | TCT | TTG | AGA | 655 |
|-----|-----|-----|-----|-----|-----|-----|-----|-----|-----|-----|-----|-----|-----|-----|-----|-----|
| Arg | Gln | Leu | Ala | Lys | Ile | Val | Lys | Ala | Asp | Arg | Arg | Gln | Ser | Leu | Arg | |
| | | | | 75 | | | | | 80 | | | | | 85 | | |

| AAT | TTG | GCT | TCT | AAG | TGG | TCG | CAG | ACA | ATT | GGC | AAA | ACT | GTC | AAG | CGA | 703 |
|-----|-----|-----|-----|-----|-----|-----|-----|-----|-----|-----|-----|-----|-----|-----|-----|-----|
| Asn | Leu | Ala | Ser | Lys | Trp | Ser | Gln | Thr | Ile | Gly | Lys | Thr | Val | Lys | Arg | |
| | | | 90 | | | | | 95 | | | | | 100 | | | |

| GAG | TGG | ACG | CGA | CAG | CAA | TTA | AAA | AGT | ATT | GGA | TAT | GGT | TTT | TAT | AAA | 751 |
|-----|-----|-----|-----|-----|-----|-----|-----|-----|-----|-----|-----|-----|-----|-----|-----|-----|
| Glu | Trp | Thr | Arg | Gln | Gln | Leu | Lys | Ser | Ile | Gly | Tyr | Gly | Phe | Tyr | Lys | |
| | | 105 | | | | | 110 | | | | | 115 | | | | |

```
GTATGTTTTG TTATTACCTG TGCATCGTAC CCAATAACTT ACTCGTAATC TTACTCGTAG      811
```

| GCC | AAG | GAA | AAA | CCC | TTG | CTT | ACG | CTT | CGT | CAA | AAA | AAG | AAG | CGT | TTG | 859 |
|-----|-----|-----|-----|-----|-----|-----|-----|-----|-----|-----|-----|-----|-----|-----|-----|-----|
| Ala | Lys | Glu | Lys | Pro | Leu | Leu | Thr | Leu | Arg | Gln | Lys | Lys | Lys | Arg | Leu | |
| | 120 | | | | | 125 | | | | | 130 | | | | | |

| CAA | TGG | GCT | CGG | GAA | AGG | ATG | TCT | TGG | ACT | CAA | AGG | CAA | TGG | GAT | ACC | 907 |
|-----|-----|-----|-----|-----|-----|-----|-----|-----|-----|-----|-----|-----|-----|-----|-----|-----|
| Gln | Trp | Ala | Arg | Glu | Arg | Met | Ser | Trp | Thr | Gln | Arg | Gln | Trp | Asp | Thr | |
| 135 | | | | | 140 | | | | | 145 | | | | | 150 | |

| ATC | ATA | TTC | AGC | GAT | GAA | GCT | AAA | TTT | GAT | GTT | AGT | GTC | GGC | GAT | ACG | 955 |
|-----|-----|-----|-----|-----|-----|-----|-----|-----|-----|-----|-----|-----|-----|-----|-----|-----|
| Ile | Ile | Phe | Ser | Asp | Glu | Ala | Lys | Phe | Asp | Val | Ser | Val | Gly | Asp | Thr | |
| | | | 155 | | | | | 160 | | | | | 165 | | | |

| AGA | AAA | CGC | GTC | ATC | CGT | AAG | AGG | TCA | GAA | ACA | TAC | CAT | AAA | GAC | TGC | 1003 |
|-----|-----|-----|-----|-----|-----|-----|-----|-----|-----|-----|-----|-----|-----|-----|-----|------|
| Arg | Lys | Arg | Val | Ile | Arg | Lys | Arg | Ser | Glu | Thr | Tyr | His | Lys | Asp | Cys | |
| | | | 170 | | | | | 175 | | | | | 180 | | | |

| CTT | AAA | AGA | ACA | ACA | AAG | TTT | CCT | GCG | AGC | ACT | ATG | GTA | TGG | GGA | TGT | 1051 |
|-----|-----|-----|-----|-----|-----|-----|-----|-----|-----|-----|-----|-----|-----|-----|-----|------|
| Leu | Lys | Arg | Thr | Thr | Lys | Phe | Pro | Ala | Ser | Thr | Met | Val | Trp | Gly | Cys | |
| | | 185 | | | | | 190 | | | | | 195 | | | | |

| ATG | TCT | GCC | AAA | GGA | TTA | GGA | AAA | CTT | CAT | TTC | ATT | GAA | GGG | ACA | GTT | 1099 |
|-----|-----|-----|-----|-----|-----|-----|-----|-----|-----|-----|-----|-----|-----|-----|-----|------|
| Met | Ser | Ala | Lys | Gly | Leu | Gly | Lys | Leu | His | Phe | Ile | Glu | Gly | Thr | Val | |
| | 200 | | | | | 205 | | | | | 210 | | | | | |

| AAT | GCT | GAA | AAA | TAT | ATT | AAT | ATT | TTA | CAA | GAT | AGT | TTG | TTG | CCA | TCA | 1147 |
|-----|-----|-----|-----|-----|-----|-----|-----|-----|-----|-----|-----|-----|-----|-----|-----|------|
| Asn | Ala | Glu | Lys | Tyr | Ile | Asn | Ile | Leu | Gln | Asp | Ser | Leu | Leu | Pro | Ser | |
| 215 | | | | | 220 | | | | | 225 | | | | | 230 | |

| ATA | CCA | AAA | CTA | TCA | GAT | TGC | GGT | GAA | TTC | ACT | TTT | CAG | CAG | GAC | GGA | 1195 |
|-----|-----|-----|-----|-----|-----|-----|-----|-----|-----|-----|-----|-----|-----|-----|-----|------|
| Ile | Pro | Lys | Leu | Ser | Asp | Cys | Gly | Glu | Phe | Thr | Phe | Gln | Gln | Asp | Gly | |
| | | | | 235 | | | | | 240 | | | | | 245 | | |

| GCA | TCA | TCG | CAC | ACA | GCC | AAG | CGA | ACC | AAA | AAT | TGG | CTG | CAA | TAT | AAT | 1243 |
|-----|-----|-----|-----|-----|-----|-----|-----|-----|-----|-----|-----|-----|-----|-----|-----|------|
| Ala | Ser | Ser | His | Thr | Ala | Lys | Arg | Thr | Lys | Asn | Trp | Leu | Gln | Tyr | Asn | |
| | | | 250 | | | | | 255 | | | | | 260 | | | |

| CAA | ATG | GAG | GTT | TTA | GAT | TGG | CCA | TCA | AAT | AGT | CCA | GAT | CTA | AGC | CCA | 1291 |
|-----|-----|-----|-----|-----|-----|-----|-----|-----|-----|-----|-----|-----|-----|-----|-----|------|
| Gln | Met | Glu | Val | Leu | Asp | Trp | Pro | Ser | Asn | Ser | Pro | Asp | Leu | Ser | Pro | |
| | | 265 | | | | | 270 | | | | | 275 | | | | |

```
ATT  GAA  AAT  ATT  TGG  TGG  CTA  ATG  AAA  AAC  CAG  CTT  CGA  AAT  GAG  CCA     1339
Ile  Glu  Asn  Ile  Trp  Trp  Leu  Met  Lys  Asn  Gln  Leu  Arg  Asn  Glu  Pro
     280                 285                      290

CAA  AGG  AAT  ATT  TCT  GAC  TTG  AAA  ATC  AAG  TTG  CAA  GAG  ATG  TGG  GAC     1387
Gln  Arg  Asn  Ile  Ser  Asp  Leu  Lys  Ile  Lys  Leu  Gln  Glu  Met  Trp  Asp
295                      300                 305                          310

TCA  ATT  TCT  CAA  GAG  CAT  TGC  AAA  AAT  TTG  TTA  AGC  TCA  ATG  CCA  AAA     1435
Ser  Ile  Ser  Gln  Glu  His  Cys  Lys  Asn  Leu  Leu  Ser  Ser  Met  Pro  Lys
               315                           320                     325

CGA  GTT  AAA  TGC  GTA  ATG  CAG  GCC  AAG  GGC  GAC  GTT  ACA  CAA  TTC          1480
Arg  Val  Lys  Cys  Val  Met  Gln  Ala  Lys  Gly  Asp  Val  Thr  Gln  Phe
               330                      335                     340

TAATATTAAT  TAAATTATTG  TTTTAAGTAT  GATAGTAAAT  CACATTACGC  CGCGTTCGAA              1540

TTAATAGTGG  TCACTTTTTT  CTTATCTCTT  AAGCAAACCG  TTTGAATAAA  TTACTCATAT              1600

TTTGTTGTT   GTTGGAAATA  GAGCAAAACT  TTTTTTTTCG  TCGTGAAGAG  AATAAAATTC              1660

TCTTTGAGAC  GAAATGCATT  GGTATGTGTT  ATCTTTAGTA  GTATTGATAA  TATAGTGTGT              1720

TAAACATTGC  GCACTGCAAA  AAAAACATGC  TGTTCGAATT  AATAGTGGTT  GGGGCTCGT               1779
```

( 2 ) INFORMATION FOR SEQ ID NO:9:

( i ) SEQUENCE CHARACTERISTICS:
        ( A ) LENGTH: 341 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met  Val  Arg  Gly  Lys  Pro  Ile  Ser  Lys  Glu  Ile  Arg  Val  Leu  Ile  Arg
 1              5                    10                       15

Asp  Tyr  Phe  Lys  Ser  Gly  Lys  Thr  Leu  Thr  Glu  Ile  Ser  Lys  Gln  Leu
               20                    25                       30

Asn  Leu  Pro  Lys  Ser  Ser  Val  His  Gly  Val  Ile  Gln  Ile  Phe  Lys  Lys
               35                    40                       45

Asn  Gly  Asn  Ile  Glu  Asn  Asn  Ile  Ala  Asn  Arg  Gly  Arg  Thr  Ser  Ala
     50                    55                       60

Ile  Thr  Pro  Arg  Asp  Lys  Arg  Gln  Leu  Ala  Lys  Ile  Val  Lys  Ala  Asp
65                   70                      75                            80

Arg  Arg  Gln  Ser  Leu  Arg  Asn  Leu  Ala  Ser  Lys  Trp  Ser  Gln  Thr  Ile
               85                    90                       95

Gly  Lys  Thr  Val  Lys  Arg  Glu  Trp  Thr  Arg  Gln  Leu  Lys  Ser  Ile
               100                   105                      110

Gly  Tyr  Gly  Phe  Tyr  Lys  Ala  Lys  Glu  Lys  Pro  Leu  Leu  Thr  Leu  Arg
          115                   120                      125

Gln  Lys  Lys  Lys  Arg  Leu  Gln  Trp  Ala  Arg  Glu  Arg  Met  Ser  Trp  Thr
     130                  135                      140

Gln  Arg  Gln  Trp  Asp  Thr  Ile  Ile  Phe  Ser  Asp  Glu  Ala  Lys  Phe  Asp
145                            150                 155                      160

Val  Ser  Val  Gly  Asp  Thr  Arg  Lys  Arg  Val  Ile  Arg  Lys  Arg  Ser  Glu
                    165                      170                 175

Thr  Tyr  His  Lys  Asp  Cys  Leu  Lys  Arg  Thr  Thr  Lys  Phe  Pro  Ala  Ser
               180                      185                      190

Thr  Met  Val  Trp  Gly  Cys  Met  Ser  Ala  Lys  Gly  Leu  Gly  Lys  Leu  His
          195                      200                      205

Phe  Ile  Glu  Gly  Thr  Val  Asn  Ala  Glu  Lys  Tyr  Ile  Asn  Ile  Leu  Gln
     210                      215                      220
```

```
Asp  Ser  Leu  Leu  Pro  Ser  Ile  Pro  Lys  Leu  Ser  Asp  Cys  Gly  Glu  Phe
225                      230                      235                      240

Thr  Phe  Gln  Gln  Asp  Gly  Ala  Ser  Ser  His  Thr  Ala  Lys  Arg  Thr  Lys
                    245                      250                      255

Asn  Trp  Leu  Gln  Tyr  Asn  Gln  Met  Glu  Val  Leu  Asp  Trp  Pro  Ser  Asn
               260                      265                      270

Ser  Pro  Asp  Leu  Ser  Pro  Ile  Glu  Asn  Ile  Trp  Trp  Leu  Met  Lys  Asn
          275                      280                      285

Gln  Leu  Arg  Asn  Glu  Pro  Gln  Arg  Asn  Ile  Ser  Asp  Leu  Lys  Ile  Lys
     290                      295                      300

Leu  Gln  Glu  Met  Trp  Asp  Ser  Ile  Ser  Gln  Glu  His  Cys  Lys  Asn  Leu
305                      310                      315                      320

Leu  Ser  Ser  Met  Pro  Lys  Arg  Val  Lys  Cys  Val  Met  Gln  Ala  Lys  Gly
               325                      330                      335

Asp  Val  Thr  Gln  Phe
               340
```

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:10:

```
Met  Val  Trp  Gly  Cys
1                    5
```

( 2 ) INFORMATION FOR SEQ ID NO:11:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:11:

```
Trp  Pro  Ser  Gln  Ser  Pro  Asp  Leu
1                    5
```

( 2 ) INFORMATION FOR SEQ ID NO:12:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:12:

```
Trp  Pro  Ser  Asn  Ser  Pro  Asp  Leu
1                    5
```

EUKARYOTIC TRANSPOSABLE ELEMENT

This application is a continuation-in-part of U.S. Ser. No. 08/239,765, filed May 9, 1994, which is a divisional of U.S. Ser. No. 07/946,237, filed Sep. 14, 1992 (now U.S. Pat. No. 5,348,874), the entire teachings of which are incorporated herein by reference.

BACKGROUND OF THE INVENTION

The Tc1-like family of transposons and the retroviral-like transposons are unique for their wide dispersion in diverse organisms. Six members belonging to the Tc-1-like family have been characterized in nematodes, diptera and fish: Tc1 in *Caenorhabditis elegans,* TCb1 in *Caenorhabditis briggsae,* HB1 in *Drosophila melanogaster,* Uhu in *Drosophila heteroneura,* Minos in *Drosophila hydei* and Tes1 in the Pacific hagfish *Eptatetrus stouti*. All are characterized by a relative short length (1.6 to 1.8 kb), the presence of inverted terminal repeats, and significant sequence similarity in the region between the repeats.

The Minos-1 transposable element has been identified as a 1775 bp dispersed repetitive sequence inserted within the transcribed spacer in one of the repeats of *Drosophila hydei* (Franz and Savakis, *Nucl. Acids Res.* 19: 6646 (Dec. 11, 1991)). The element is characterized by 255-bp long perfect inverted repeats and the presence of two long, non-overlapping open reading frames (ORFs) on the same strand. The longest of the ORFs shows approximately 30% sequence identity with TcA, but does not begin with an ATG codon. It appears, therefore, that the cloned element represents a defective member of the Minos family, as is the case with all previously sequenced Tc1-like elements, with the possible exceptions of Tc1 and TCb1.

SUMMARY OF THE INVENTION

The invention relates to an isolated transposable element, or an isolated DNA sequence which encodes a transposase protein (or a portion of a transposase protein). The isolated transposable element or the isolated DNA sequence is characterized by the ability to hybridize to the DNA sequence of Minos 1 under stringent hybridization conditions. The invention also relates to a purified transposase protein, or peptide fragments thereof, encoded by such DNA sequences.

In another aspect, the invention relates to a method for the stable introduction of a DNA sequence of interest into a cell. This method involves the use of an isolated transposable element of the type described in the preceding paragraph, the isolated transposable element being modified to include the DNA sequence of interest flanked by the termini of the isolated transposable element. This modified transposable element is introduced into the cell in the presence of a transposase protein, or a DNA sequence encoding a transposase protein. The role of the transposase protein is to catalyze the transposition of the modified transposable element containing the DNA sequence of interest into the genomic DNA of the cell.

In a third aspect, the invention relates to a method for isolating members of the Tc-1 family of transposable elements from genomic DNA of a eukaryote of interest. According to this method, oligonucleotide primers are provided which are complementary to a sequence of at least about 12 consecutive nucleotides which encode amino acids which are highly conserved in aligned sequences of nematode Tc-1 family members and Minos family members. These oligonucleotide primers are used to prime amplification by the polymerase chain reaction (PCR). The amplification products are then used to isolate DNA encoding the entire Tc-1 family member from the eukaryote of interest by conventional methods.

In a fourth aspect, the invention relates to a transgenic animal. The transgenic animal is produced by a method which involves the use of an isolated transposable element characterized by the ability to hybridize to the DNA sequence of Minos 1, the isolated transposable element being modified to include the DNA sequence of interest flanked by the termini of the isolated transposable element. This modified transposable element is introduced into a cell in the presence of a transposase protein, or a DNA sequence encoding a transposase protein.

BRIEF DESCRIPTION OF THE DRAWING

FIGS. 1A–1C is a diagram providing the consensus sequence of elements Minos-1, Minos-2 and Minos-3 with nucleotide deletions after nucleotides 365, 678 and 715. The terminal inverted repeats and the intron sequence are shown in small letters. Differences between the three elements are indicated above and below the nucleotide sequence. More specifically, nucleotide 896 is a G in Minos-2 and Minos-3 and an A in Minos-1. Nucleotide 1157 is a C in Minos-1 and Minos-3 and a T in Minos-2.

FIGS. 2A–2C is a diagram providing the consensus sequence of elements Minos-1, Minos-2 and Minos-3. The terminal inverted repeats and the intron sequence are shown in small letters. The first and last nucleotides of the sequence, A and T, respectively, are generated by a duplication of the chromosomal target site TA during insertion of the element. The deduced amino acid sequence of two open reading frames is shown above the nucleotide sequence. Differences between the three elements are indicated above and below the nucleotide sequence. More specifically, nucleotide 900 is a G in Minos-2 and Minos-3 and an A in Minos-1. Nucleotide 1161 is a C in Minos-1 and Minos-3 and a T in Minos-2. Amino acid residue 148 is a tryptophan in Minos-2 and Minos-3 and a stop codon in Minos-1. Amino acid residue 235 is a serine in Minos-1 and Minos-3 and a leucine in Minos-2.

SEQUENCE LISTING CROSS-REFERENCE

Figure 3A:
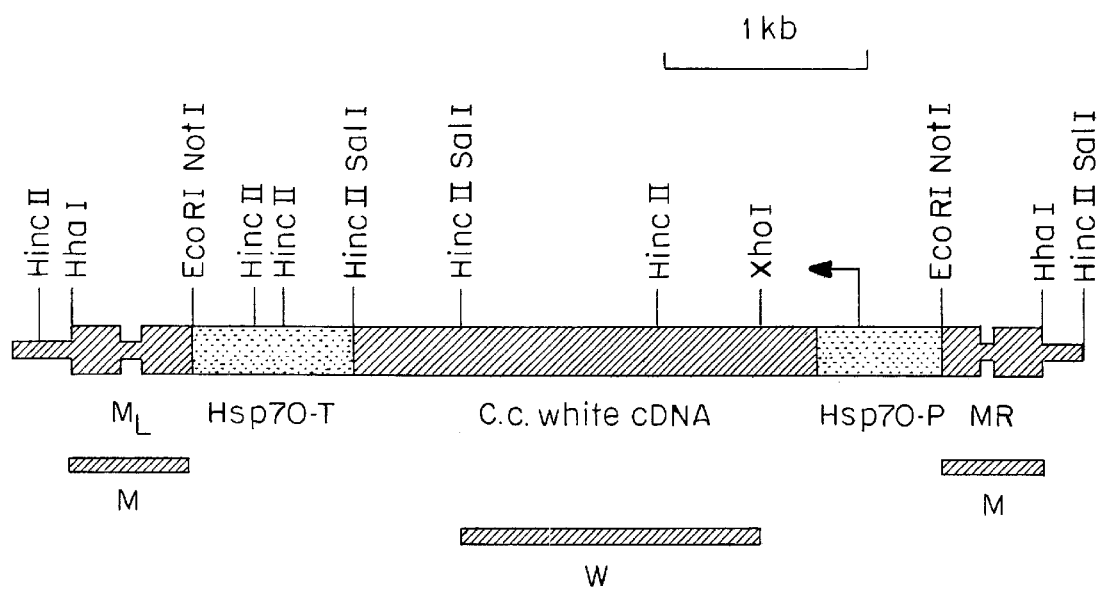
FIG. 3A is a diagram of the insert of the transposon plasmid pMihsCcw. ML and MR signify the left- and right-end parts of Minos, respectively. Speckled boxes indicate the *D. melanogaster* Hsp70 promoter (Hsp70-P) and terminator (Hsp70-T) sequences. Wide hatched bars indicate the Minos (M) and Medfly white (W) sequences that were used as probes for the analysis of transformants.

In portions of the Specification, the following sequence listing cross-reference is applicable:

| SEQ ID NO: 1 | Nucleic acid sequence of Minos-1 with nucleotide deletions after nucleotides 365, 678 and 715. |
|---|---|
| SEQ ID NO: 2 | Nucleic acid sequence of Minos-2 with nucleotide deletions after nucleotides 365, 678 and 715. |
| SEQ ID NO: 3 | Nucleic acid sequence of Minos-3 with nucleotide deletions after nucleotides 365, 678 and 715. |
| SEQ ID NO: 4 | Nucleic acid sequence of Minos-1. |
| SEQ ID NO: 5 | Deduced amino acid sequence of Minos-1. |
| SEQ ID NO: 6 | Nucleic acid sequence of Minos-2. |
| SEQ ID NO: 7 | Deduced amino acid sequence of Minos-2. |
| SEQ ID NO: 8 | Nucleic acid sequence of Minos-3. |
| SEQ ID NO: 9 | Deduced amino acid sequence of Minos-3. |
| SEQ ID NO: 10 | MVWGC. |
| SEQ ID NO: 11 | WPSQSPDL. |
| SEQ ID NO: 12 | WPSNSPDL. |

DETAILED DESCRIPTION OF THE INVENTION

The invention disclosed herein is based on the initial discovery of Minos-1, an apparently defective member of the Tc-1 family of transposable elements. This 1779-bp element is characterized by perfect inverted repeats of 255-bp at each termini. The sequence encodes two non-overlapping reading frames, one of which has significant similarity with the putative transposase encoded by the transposable element Tc1 of Caenorhabditis elegans. However, the Minos-1 element, because of a stop codon within the putative transposase gene, apparently cannot encode an active transposase.

In an effort to identify sequences related to the Minos-1 sequence, genomic DNA of D. hydei was probed with a portion of the Minos-1 sequence under stringent hybridization conditions. As discussed in detail in the Exemplification section which follows, two full-length related sequences were identified, both of which encode an active transposase.

Isolated Nucleic Acids and Uses Thereof

Thus, in one aspect, the subject invention relates to an isolated transposable element which hybridizes to the DNA sequence of Minos-1 under stringent hybridization conditions. As used herein, stringent hybridization conditions are considered to be hybridization in a buffered solution of 0.9M NaCl at 55° C. In D. hydei there are up to 30-copies detected which hybridize to Minos thus, it is likely that a large number of variants can be isolated using these conditions. Comparable hybridization stringency can be established at other salt concentrations and temperatures. This is accomplished, for example, by the inclusion of organic denaturants such as formamide in the hybridization buffer. DNA sequences which hybridize to the Minos-1 sequence under stringent hybridization conditions are referred to herein as members of the Minos family of transposable elements. DNA sequences which hybridize to the Minos-1 sequence under stringent hybridization conditions include, for example, the Minos-2 and Minos-3 DNA sequences. Other examples of DNA sequences which hybridize to the Minos-1 sequence under stringent hybridization conditions include Minos-1, Minos-2 and Minos-3 DNA sequences having base deletions, insertions and/or substitutions.

The term transposable element, as used herein, refers to a DNA sequence whose excision from/insertion into genomic DNA is catalyzed by a functional transposase protein encoded by a non-defective member of the Minos family of transposable elements. A member of the Minos family which encodes a functional transposase and possesses other necessary cis-acting elements (e.g., inverted terminal repeats) falls within this definition. In addition, a transposable element which encodes a defective transposase (e.g., Minos-1 itself) falls within this definition. As discussed in greater detail below, such defective transposable elements can be used in conjunction with a helper element (i.e., a member of the Minos family which encodes a functional transposase) to introduce a DNA sequence of interest into a cell (e.g., a eukaryotic cell such as an animal, plant or yeast cell or a prokaryotic cell such as a bacterial cell).

The invention also relates to an isolated DNA sequence encoding a functional transposase protein, or a portion of a transposase protein, encoded by a member of the Minos family. Such a DNA sequence need not retain the ability to transpose in the presence of the encoded transposase protein. A sequence encoding a functional transposase protein can be used to prepare an expression construct which can be used to produce the transposase protein by recombinant DNA methodology. Such a recombinant protein can be over-produced in a eukaryotic (e.g., yeast) or prokaryotic host cell (e.g., E. coli), and subsequently purified by conventional methods.

The active transposase can be used in a variety of ways. For example, as discussed below, the transposase can be co-introduced into a eukaryotic cell with a modified transposon carrying a DNA sequence of interest to catalyze the insertion of the modified transposon into the genomic DNA of the eukaryotic cell. This is an alternative to the co-introduction of a helper construct in eukaryotic cells which do not constitutively produce the Minos transposase.

In addition, the transposase, or portions thereof, can be used to produce antibodies (monoclonal and polyclonal) reactive with the transposase protein. Methods for the production of monoclonal and polyclonal antibodies are straightforward once a purified antigen is available.

Through the isolation and DNA sequence analysis of additional members of the Minos family, refinement of the consensus sequence of FIGS. 2A–2C is possible. This refined consensus sequence can be used to predict modifications of the transposase protein which will affect the specific activity of the transposase. Such predictions are easily tested by modifying the DNA sequence of an expression construct encoding the transposase by site-directed mutagenesis to either bring the sequence into a greater degree of conformance with the consensus sequence, or a lesser degree of conformance with the consensus sequence. The affect of such changes on the activity of the transposase protein are monitored by assessing the affect of the mutation on transposition frequency catalyzed by the recombinant transposase.

Methods for the Introduction of DNA Sequences into a Cell

Transposable elements of the Minos family, and the active transposase encoded by such elements, are useful in methods for introducing a DNA sequence of interest into a cell (e.g., a eukaryotic cell such as an animal, plant or yeast cell or a prokaryotic cell such as a bacterial cell). Typically, the DNA sequence of interest will be a gene which encodes a protein. Such a gene can be placed under the regulatory control of a promoter which can be induced or repressed, thereby offering a greater degree of control with respect to the level of the protein in the cell. In addition to a DNA sequence encoding a protein, any other DNA sequence can be introduced by this method including, for example, regulatory sequences.

The Minos transposable elements can be used to introduce a DNA sequence of interest into the cells of invertebrates. For example, the Minos transposable elements can be used to introduce a DNA sequence of interest into the cells of arthropods. Arthropods include, for example, crustaceans, arachnids, myriapods and insects.

The Minos transposable elements can be used to introduce a DNA sequence of interest into either germ line or somatic cells. The introduction of DNA into germ line cell has the significant advantage that the DNA sequence of interest will be contained in all cells of the mature organism and transmitted to progeny.

The Minos transposable element has been demonstrated to function in a species which is separated from the Minos source species by an evolutionary distance of 40 million years. This represents the first demonstration of a mobile element which can function autonomously in the germ line of eukaryotes separated by such an evolutionary distance and is likely to lead to the development of a long-sought transformation system applicable across taxonomic barriers.

However, even within the dipteran class, significant important applications for the Minos element exist. Listed below are examples of a variety of plant and animal pests, and human disease vectors which fall within the dipteran genus.

|  | Common Name |
|---|---|
| Agricultural Pests | |
| Ceratitis capitata | Medfly |
| Anastrepha species | Carribean fruit fly |
| Dacus oleae | Dacus |
| Bactrocere species | Oriental fruit fly |
| Animal Pests | |
| Cochliomya hominivorax | Screw Worm Fly |
| Lucilia cuprina | Sheep blowfly |
| Simulium species | Black fly |
| Human Disease Vectors | |
| Anopheles species | mosquito |
| Aedes species | mosquito |
| Musca domestica | house fly |

Methods currently employed to control the populations of certain members of the dipteran class include the release of sterile males. An example of the utility of the germ line transformation methods of this invention includes the improvement of the existing release method. The methods of this invention can be used to improve such methods by enabling sexing schemes and for developing strains with desired characteristics (e.g., improved viability in the field), conditional lethal genes for improved safety, and visible or molecular genetic markers for monitoring. Genetic sexing, i.e. the capability of selectively killing the females (or transforming them into males) in mass-rearing facilities, is recognized as an important need presently. Rearing and releasing only males has several advantages including lower breeding cost and the avoidance of population explosions due to inadvertent release of non-sterilized insects.

For example, the Mediterranean fruit fly (Medfly) *Ceratitis* (*C.*) *capitata* is a major agricultural pest for many fruit species that is geographically widespread in tropical and temperate regions. The Medfly has been introduced relatively recently into the New World, and appears to be spreading rapidly, threatening fruit producing areas in North America (Carey, J. R., *Science* 253: 1369 (1991)). Since the mid 1970's, the sterile insect technique has been used successfully for Medfly eradication and control. This method relies on the decrease in or collapse of fly populations following releases of large numbers of sterile insects over infested areas, and offers an environmentally attractive alternative to massive spraying with insecticides (Knipling, E. F., *Science* 130: 902 (1959)). The germ line transformation methods of this invention can be used to improve the sterile insect technique by, for example, enabling sexing schemes. The germ line transformation methods of this invention can also be used for developing Medfly strains with desired visible markers that can be used for monitoring effective population control.

The methods are also useful for insects for which it might be desirable to introduce new traits in the genetic pool, rather than controlling the population levels. For example, the presence of several sympatric sub-species of *Anopheles gambiae*, all of which transmit malaria, makes it highly unlikely that population control with biological methods such as the sterile insect technique will work. An alternative scheme might involve spreading genes for refractoriness to parasite infection into the existing populations of Anopheles through the use of transposable elements. Population dynamics simulations indicate that this can be effected by releasing relatively small numbers of individuals carrying an autonomously transposing element.

The element may be actively transposing in other taxa (e.g. vertebrates) under the appropriate conditions thus, it will be recognized by those skilled in the art that the methods disclosed herein relating to diptera can be extended to higher eukaryotes. If the transposase is functional when expressed or otherwise introduced in vertebrate embryos or cells, it is possible to develop transformation methods based on Minos elements for non-insect species as well.

A transposon-based method for producing transgenic animals or for stably transfecting cells in vitro has very important advantages compared to the methodology presently used. For example, stable integration of DNA into the germline of several mammals is now routinely achieved by micro-injecting linear DNA molecules into the nucleus of early embryos. Some of the animals that develop from injected embryos are mosaics for integration events and in only a fraction of these the germ line is involved. Moreover, most events consist of integration of tandem repeats of the injected DNA; single-insertion events do occur at higher frequencies relative to tandem insertions if DNA is injected at lower concentrations, but at a considerable cost in time and expense because the overall transformation frequencies drop.

Using a defined transposon-transposase system may overcome some or all of these problems. First, as in Drosophila, it may not be necessary to have to inject the DNA into the nucleus. If a mixture of transposon plus helper plasmids (or transposon plus purified transposase) is active when introduced into the cytoplasm, it may be possible to replace costly and time-consuming microinjection with other methods, such as use of liposomes. Second, by controlling the relative transposon/transposase levels it may be possible to improve the overall efficiency, with a parallel increase of the frequency of single-insertion events.

Methods for the introduction of the Minos transposon into germ line cells of diptera are analogous to those previously used in connection with other transposable elements (see, e.g., *Drosophila, A Laboratory Handbook,* Ashburner, M., Cold Spring Harbor Laboratory Press, Cold Spring Harbor, N.Y., (1989)). Briefly, the most common approach is to employ a carrier/helper transposon system. The carrier transposon is a Minos transposon which has been modified by the insertion of a DNA sequence of interest in the region of the transposon flanked by the inverted terminal repeats. Typically, sequences relating to the transposase function are deleted in order to accommodate the DNA of interest. The helper transposon is a Minos transposable element which encodes an active transposase. The transposase catalyzes the transposition of the carrier transposon into the genomic DNA of the germ line eukaryotic cells. Typically, the helper and carrier are microinjected into the posterior pole of pre-blastoderm embryos, where the precursor cells of the germ line develop.

An alternative to the helper/carrier system involves the purification of active transposase (for example, from an *E. coli* culture transformed with a recombinant construct encoding the Minos transposase). The purified transposase can be co-injected into appropriately selected cells along with a carrier transposon to effect integration of the carrier into the recipient genome.

The compositions and methods of this invention are also useful for the introduction of a DNA sequence of interest into mammalian somatic cells. Typically this is accomplished in a manner analogous to the methods described in connection with germ line cells (e.g., helper/carrier systems are employed). Somatic cell introduction is typically carried out using cells grown in culture and DNA can be introduced, for example, by calcium co-precipitation or other conventional methods.

Methods for Isolating Additional Tc-1 Family Members

DNA sequence analysis of the members of the Minos family disclosed herein, and comparison of this sequence information to the sequences of Tc-1 family members from evolutionarily distant organisms (e.g., nematode), reveal short stretches of conserved amino acid sequence within the transposase coding region. This high degree of conservation suggests a method for isolating Tc-1 family members from diverse eukaryotic species.

This method involves the amplification of DNA by polymerase chain reaction from a eukaryote of interest using primers which are complementary to a sequence of at least about 12 consecutive nucleotides which encode amino acids which are highly conserved in aligned sequences of nematode Tc-1 family members and dipteran Minos family members. Such amino acid sequences include, for example, MVWGC (SEQ ID NO:10), WPSQSPDL (SEQ ID NO:11) and WPSNSPDL (SEQ ID NO:12).

EXEMPLIFICATION

Materials and Methods

Fly strains. Standard procedures were used for culturing of *Drosophila hydei*. All strains used in this study have been used previously for rDNA work and are named for the X and Y chromosomes. Strain bb$^1$ (bb$^1$/bb$^1$×bb$^1$/Y) carries a bobbed X chromosome; strain X$^7$ (X$^7$/X$^7$×X$^7$/Y) is a subline of the Dusseldorf wild-type strain; strain X^X/Y(X^X/Y×X/Y) females carry a compound X chromosome which has no rDNA. Strain wm1/Y (wm1/Y×X-3/Y) females have a compound X chromosome (wm1); males carry a X-autosome 3 translocation which has no rDNA.

DNA manipulations and sequencing. All basic procedures were carried out essentially as described (Maniatis et al. 1982). DNA from adult females of strain bb$^1$ was partially digested with EcoRI and cloned into phage vector λgt7. To recover new Minos elements, the library was screened by hybridization with a 1.7 kb HhaI fragment which contains most of the Minos-1 sequence. For sequencing, the appropriate restriction fragments from positive clones were subcloned into plasmid vectors pUC8 and pUC9 and nested deletions were generated by digestion with exonuclease Bal31 followed by subcloning. Sequencing was performed by conventional methods. Both strands were sequenced, with a minimum of two independent sequences for each base pair.

Sequence analysis. Database searches and sequence analysis and manipulations were performed using programs FASTA (Pearson and Lipman, *Proc. Natl. Acad. Sci. USA* 85:2444–2448 (1988)). BLAST (Altschul et al., *J. Mol. Biol.* 215:403–410 (1990)) and the computer package GCG (Devereux et al., *Nuc. Acids Res.* 12:387–395 (1984)). The program CLUSTAL (Higgins and Sharp, 1988) was used for protein sequence alignments.

Results

The Sequence of Minos. Three new representatives of the Minos family of transposable elements have been cloned and sequenced; they have been named Minos-2, Minos-3 and Minos-4, Minos-1 being the element reported previously. Minos-2 and Minos-3 are complete elements distinct from Minos-1, as judged from the restriction maps of the flanking DNA and the flanking sequences. The sequences of the elements, summarized in FIGS. 2A–2C, show very little variation, differing in only two positions. At position 900 of the sequence, Minos-2 and Minos-3 have a G instead of the A found in Minos-1. This transition changes a TAG stop codon to TGG and restores a 603 bp ORF beginning with ATG at position 878. The second difference is at nucleotide 1161, which is a C in Minos-1 and Minos-3 and a T in Minos-2. This causes a ser→leu substitution in ORF2 of Minos-2, relative to Minos-1 and Minos-3. Minos-2 and Minos-3, therefore, have two complete ORFs beginning with an ATG; ORF1, which can encode a 133 amino-acid peptide, and ORF2, which can encode a 201 amino-acid peptide.

The Minos-4 clone does not contain a complete element. The sequence of the cloned DNA fragment begins at the EcoRI site found at position 1172 of the other members and is identical to the Minos-1 sequence to base 1779. Apparently Minos-4 represents a partial isolate rather than a defective member of the family, since the library from which it was isolated was from DNA cut with EcoRI.

The DNA sequence flanking the cloned elements are different from each other; this indicates that these elements are inserted at different sites of the *D. hydei* genome, and are, therefore, distinct. These sequences are mainly characterized by a high A/T content, and do not show any other obvious similarity. In all cases, the inverted repeats end with the dinucleotide TA, which is at the same time a direct and an inverted repeat. Because of this, there is some ambiguity in defining the ends of the element precisely. Shown below are the sequences of the Minos 1–4 insertions sites. The rDNA sequences flanking the Minos elements are shown in lower case and Minos sequences are shown in upper case. The rDNA sequence identical to the flanking DNA of Minos-1 has been aligned with the Minos-1 insertion sequence. It is noted that since gapped sequences are treated as separate sequences for purposes of the Rules of Practice in Patent Cases (37 CFR 1.822(o)), and since each of the separate sequences contain less than 10 nucleotides, the sequences shown below have not been listed in the Sequence Listing.

In the case of Minos-1, which is inserted into a region which has been previously sequenced, the external transcribed spacer of the rDNA repeat, there are two possibilities. As shown below, deleting the sequence which begins with ACGA and end with TCGT would restore the rDNA sequence; the element, with an A and a T at the two ends may have inserted between a T and an A. In this possibility, the element would be 1779 bp long with 255 bp inverted repeats. Alternatively, the element may begin and end with CGA . . . TCG and produce a target site duplication, as happens with many other mobile elements. In this possibility the target site duplication would involve the dinucleotide TA, and the size of the element would be 1777 bp. For numbering, the A of the TA repeat has been designated nucleotide number 1 of the Minos-1–3 sequences.

```
rDNA      ataat--------------------------attaa
Minos-1   ataatACGA---------TCGTattaa
Minos-2   aaatatACGA---------TCGTataat
Minos-3   gctttACGA---------TCGTagaag
Minos-4   ttctACGA
          |                          |
          1775                       1
```

Mobility and homogeneity of Minos elements. The striking degree of sequence conservation among the cloned Minos elements suggests that, as in the case of Tc1, all Minos elements may be highly homogeneous. To test this the single HhaI site within each of the terminal repeats of Minos was exploited. The 1.68 kB HhaI fragment of Minos-1 was used as probe in a Southern blot of genomic DNA from the same strains, digested with CfoI, an isoschisomer of HhaI. A single, strong band of approximately 1.7 kb was detectable in all lanes, indicating that no major deletions or rearrangements are present in the Minos elements present in these strains.

Comparison of the proteins encoded by Tc1 and Minos. The deduced 201 amino acid sequence of the ORF2 in Minos-2 and Minos-3 shows significant sequence similarity with the 201 carboxy terminal residues of TcA, the putative transposase of Tc1; alignment of the sequences gives 63 identities (31%) and 91 conservative substitutions (45%) with only two single-residue insertion-deletions. The two sequences, however, differ in size; TcA has 72 additional amino acids at the amino end. The 50 amino-terminal residues of TcA show weak but significant sequence similarity with the carboxy terminus of Minos ORF2; introduction of a 60-bp deletion in the Minos DNA sequence creates a long open reading frame which contains most of ORF1 (codons 1 to 138) and the entire ORF2 extended by 22 codons upstream of the ATG. Interestingly, this 60-bp sequence, from base 752 to base 811 of the Minos sequence, exhibits features of an intron. More specifically, the 5' and 3' ends conform to the consensus splice donor and acceptor sites and a version of the internal splice signal consensus is found 30 nucleotides upstream from the 3' end.

Divergence of the TcA-related sequences. Although Minos inhabits a Drosophila species, it is not more related to the other Tc1-like elements from Drosophila species, HB1 and Uhu. These elements, or at least the members which have been sequenced, do not contain open reading frames comparable in length to that of Tc1. However, if small numbers of deletions and insertions are introduced in their DNA sequences, open reading frames can be generated which show significantly similarity with the TcA sequence. Most of these insertion-deletion changes involve one nucleotide, presumably representing mutations which have accumulated in these inactive elements. Table 1 shows a similarity matrix between the three Drosophila and the two nematode elements, in the regions corresponding to the hypothetical Minos exon 2. In Table 1, percent identities are shown above the diagonal; identical/total positions are shown below the diagonal. Minos shows approximately the same degree of similarity (between 28 and 36 percent identity) with all the other elements; HB1 and Uhu show comparable similarities. In a multiple sequence alignment of the same regions, 21 of the resulting 225 positions (9%) are invariant and 49 positions (22%) are occupied by related amino acids. It should also be noted that the similarity between HB1 and Uhu with Tc1 and Minos extends another 18 codons upstream from the position corresponding to the first codon of the hypothetical exon 2 of Minos. No other significant similarities can be detected between Tc1, Uhu, HB1 and Minos in the sequences between the terminal repeats.

TABLE 1

|       | Tc1     | TCb1    | Minos   | Uhu     | HB1 |
|-------|---------|---------|---------|---------|-----|
| Tc1   |         | 71      | 31      | 44      | 33  |
| TCb1  | 160/223 |         | 34      | 41      | 35  |
| Minos | 70/221  | 75/222  |         | 36      | 28  |
| Uhu   | 96/217  | 89/217  | 78/218  |         | 31  |
| HB1   | 73/223  | 79/223  | 62/222  | 68/219  |     |

The ORF1 sequence is related to the paired box sequence. Searches of the nucleic acid and protein sequence data libraries with the ORF1 sequence using the FASTA and WORDSEARCH algorithms gave no significant matches. However, the Basic Local Alignment Search Tool program revealed a similarity with the paired box sequence, a peptide sequence found in the Drosophila paired gene product, and conserved in other Drosophila and mammalian genes. This similarity extends approximately between residues 1 to 96 of the Minos sequence, and residues 35 to 131 of the Drosophila paired protein. Alignment of the Minos sequence with the Drosophila and human paired box sequences for maximum similarity shows 16 invariant positions in this region (17%) and 49 positions occupied by related amino acids (51%). The corresponding values for the human and Drosophila paired sequences are 72% identities and 23% conserved positions.

Although the Minos-paired similarity is weak compared to that between the Drosophila and human paired sequences, it is statistically significant. The similarity scores between the Minos sequence (amino acids 1 to 118 of ORF1) to the corresponding human paired sequence (amino acids 17 to 135 of the published sequence) is approximately 10 standard deviations higher than the average of the scores obtained from 50 comparisons made between the Minos sequence and 50 randomly shuffled human paired sequences.

Transposition in $D.$ $melanogaster.$ A $D.$ $melanogaster$ "helper" strain which can overproduce the Minos transposase upon exposure to heat shock was constructed. The strain was constructed by introducing a modified Minos element into the germ line by conventional P element transformation (see, e.g., $Drosophila,$ $A$ $Laboratory$ $Handbook,$ Ashburner, M., Cold Spring Harbor Laboratory Press, Cold Spring Harbor, N.Y., (1989)). To place the Minos transposase under heat shock control, the left-hand terminal repeat of Minos-2 was replaced by the $D.$ $melanogaster$ hsp 70 promoter. This modified element was inserted into the P element transformation vector pDM30, which contains a wild-type copy of the Drosophila rosy (ry) gene as a dominant visible marker. The plasmid (pPhsM2) was injected into pre-blastoderm embryos of a ry strain, injected GO adults were mated to ry flies and ry$^+$ G1 progeny were bred further. Three independent transformants were recovered, two on the third chromosome (named M46 and M67) and one on the X (M84). Southern blots using ry and Minos probes indicated that each of the three transformants contains a single insertion of the complete sequence between the P element ends. Northern blots of total RNA from adult transformed flies subjected to a heat shock showed abundant transcripts hybridizing to Minos probes. No Minos-related transcripts have been detected by the same probes in RNA from non-heat shocked flies. The structure of the RNA transcripts was investigated in another series of experiments discussed below.

Breeding of these transformants showed that they are all homozygous lethal. This observation was unexpected; the recovery of recessive lethal mutations due to insertional inactivation of essential genes is a rather uncommon event in P transformation experiments. Moreover, the insertion into the X clearly has not caused a "knock-out" mutation since hemizygous males are viable and fertile; only homozygous females are inviable. This behavior suggested that the lethality may be dosage- or pairing-dependent; the latter being more likely because double heterozygotes of the two insertions in the 3rd chromosome are viable. The observed lethality is a useful feature which enables one to follow the segregation of the "helper" chromosomes by keeping them over genetically marked balancers.

Strong evidence for Minos transposition in the germ line was obtained by first introducing the M67 chromosome into a white background (y,w; TM3/M67). Pre-blastoderm embryos were injected with a plasmid (pM2w) containing a complete Minos-2 element with a wild-type copy of the white (w) gene inserted into its unique EcoRI restriction site within ORF2. The inserted w sequences provide a dominant selectable marker; in addition they interrupt ORF2, making the production of active transposase from this construct highly improbable. Three separate experiments were conducted: In experiment A injected embryos and the developing larvae and adults were kept at 18 degress C., in experiment B they were kept at 25 degress C. throughout development, and in experiment C the embryos were subjected to a 1-hour 37 degree C. heat shock three hours after injection. All emerging G0 flies (63, 38 and 61, from experiments A, B and C, respectively) were mated to y,w; TM3/Dgl3 flies and the progeny were scored for the appearance of the $w^+$ phenotype. To date, at least four independent germ line transformation events have been detected in experiments A and B. Two of these events come from a single G0 male from experiment A and at least two have been recovered from two different G0 flies from experiment B. The results are shown in Table 2 below:

TABLE 2

| Experiment | G0 | #G1 Scored | $w^+$G1 Chromosome | Insertion |
|---|---|---|---|---|
| A | A10 | 286 | A10.1 | X |
| | | | A10.2 | 3 |
| | | | A10.3 | 3 |
| | | | A10.4 | ? |
| | | | A10.5 | ? |
| | | | A10.6 | ? |
| B | B13 | 75 | B13.1–3 | ? |
| C | B33 | 116 | B33.1–18 | ? |

Evidence that the Minos-$w^+$ transposon can be mobilized in the soma of flies which produce the transposase has been obtained. Larvae of the constitution y,w; TM3/[M2w]M67 (progeny of the A10.2 fly), which contain both transposon and helper sequences, were subjected to heat shock and adult flies were examined for the appearance of eye color mosaicism. More than 50% of the flies showed mosaicism of different degrees. Patches of ommatidia with either reduced or increased pigmentation were observed which is consistent with the expected result of a somatic deletion or transposition event. No mosaicism has been detected in flies not subjected to a heat shock at the larval stage. The somatic instability results clearly indicate that the $w^+$ insertions are minos-mediated.

Analysis of Minos mRNA transcripts. Total RNA was isolated from the M67 strain, the construction of which is described above. The structure of mRNA transcripts was investigated by the polymerase chain reaction (PCR) method of DNA amplification. A particularly important aspect of this investigation was to determine the status of the 60 base pair putative intron region (discussed above) in the mRNA transcripts. As was mentioned previously, this sequence is characterized by 5' and 3' ends which conform to the consensus splice donor and acceptor sites, and has a version of the internal splice signal consensus sequence 30 nucleotides upstream from the 3' end.

To determine the status of this putative intron, PCR priming sites were selected from exon sequences (ORF1 and ORF2) flanking the putative intron. The PCR product synthesized in this reaction was cloned and sequenced by conventional methods. The sequencing experiments revealed unambiguously that the 60 base pair intron sequence was, in fact, absent in the amplified DNA.

The removal of the 60-bp sequence in the correctly spliced primary transcript initiating upstream from ORF1, results in the generation of a 1023-bp open reading frame which encodes a peptide of 341 amino acids. An alignment of the 273 carboxy-terminal amino acids of this peptide with the sequences of TcA and the 273-residue hypothetical peptide of TCb1 was generated by the multiple alignment program CLUSTAL, which introduces gaps in the sequences to achieve maximum sequence similarity. The three sequences were aligned without the need of any insertions-deletions (with the exception of the two one-residue gaps required for optimal alignment in the ORF2 region) and show an overall 28% identity, i.e. 76 of the 273 positions are invariant. In the region upstream from the first methionine of ORF2, twelve out of seventy two positions (16%) are invariant; 29 positions (40%) are occupied by structurally related amino acid residues. Although this degree of similarity is lower than that in the ORF2 region, it is statistically significant.

The sequence similarity between TcA and the carboxy end of the Minos hypothetical protein is also reflected in their secondary structures. Comparisons of α-helix and β-sheet predictions and hydrophobicity profiles between the Tc1 and Minos sequence show similarities in several regions. Another feature of the sequences is their high content, approximately 20%, in basic amino acids. TcA has 29 arginines, 16 lysines and 11 histidines, and the TcA-related Minos sequence has 20 arginines, 32 lysines and 4 histidines. These are more abundant at the amino-terminal half of both sequences, although the position of most is not strictly conserved. The proteins are fairly basic, with computed isoelectric points of 11.27 for TcA and 10.73 for the related Minos peptide. The computed pI of the complete hypothetical 361 amino acid Minos protein is 10.97.

Gene transfer into C. capitata using Minos transposable elements. Single copies of exogenous DNA can be introduced into the genome of C. capitata by using a germ line transformation system which utilizes the transposable element Minos to mediate precise integration of DNA at acceptable frequencies.

To provide an effective dominant selectable marker for detection of transformants, an approximately 3.7 kb NotI fragment containing the wild-type white cDNA of C. capitata, flanked by the D. melanogaster hsp 70 promoter and terminator sequences, was inserted into the NotI site of the Minos vector pMiNot which was constructed by replacing a 644 bp MscI fragment of the Minos transposase gene (nucleotides 618 to 1264 of FIGS. 2A–2C) with a NotI linker. This modified element (shown in FIG. 3A) was inserted into the E. coli vector pTZ18R (Pharmacia), creating a plasmid (pMihsCcw) having a wild-type copy of the *C. capitata* white (w) gene as a dominant visible marker.

To place the Minos transposase under heat shock control, the left-hand terminal repeat of Minos-2 was replaced by a 456 bp fragment containing the *D. melanogaster* hsp 70 promoter. This modified element (shown in FIG. 3B) was inserted into the *E. coli* vector pTZ18R (Pharmacia), creating the transposase-producing plasmid pHSS6hsMi.

The plasmids pMihsCcw and pHSS6hsMi were introduced into pre-blastoderm Medfly w/w embryos by a microinjection procedure similar to that used for Drosophila. For egg collecting, flies were mass-reared in population cages at 24° C. Eggs were collected at 24° C. for 60 minutes, and then were dechorionated, desiccated and microinjected at 18° C. with a mixture of 100 mg/ml helper and 400 mg/ml transposon plasmid DNA as described for Drosophila embryos (Rubin, G. M. and Spradling, A. C., *Science* 218: 348 (1982)). Modifications of the procedure were not necessary, because the eggs of the two species are similar in morphology and in resistance to desiccation.

Figure 4:
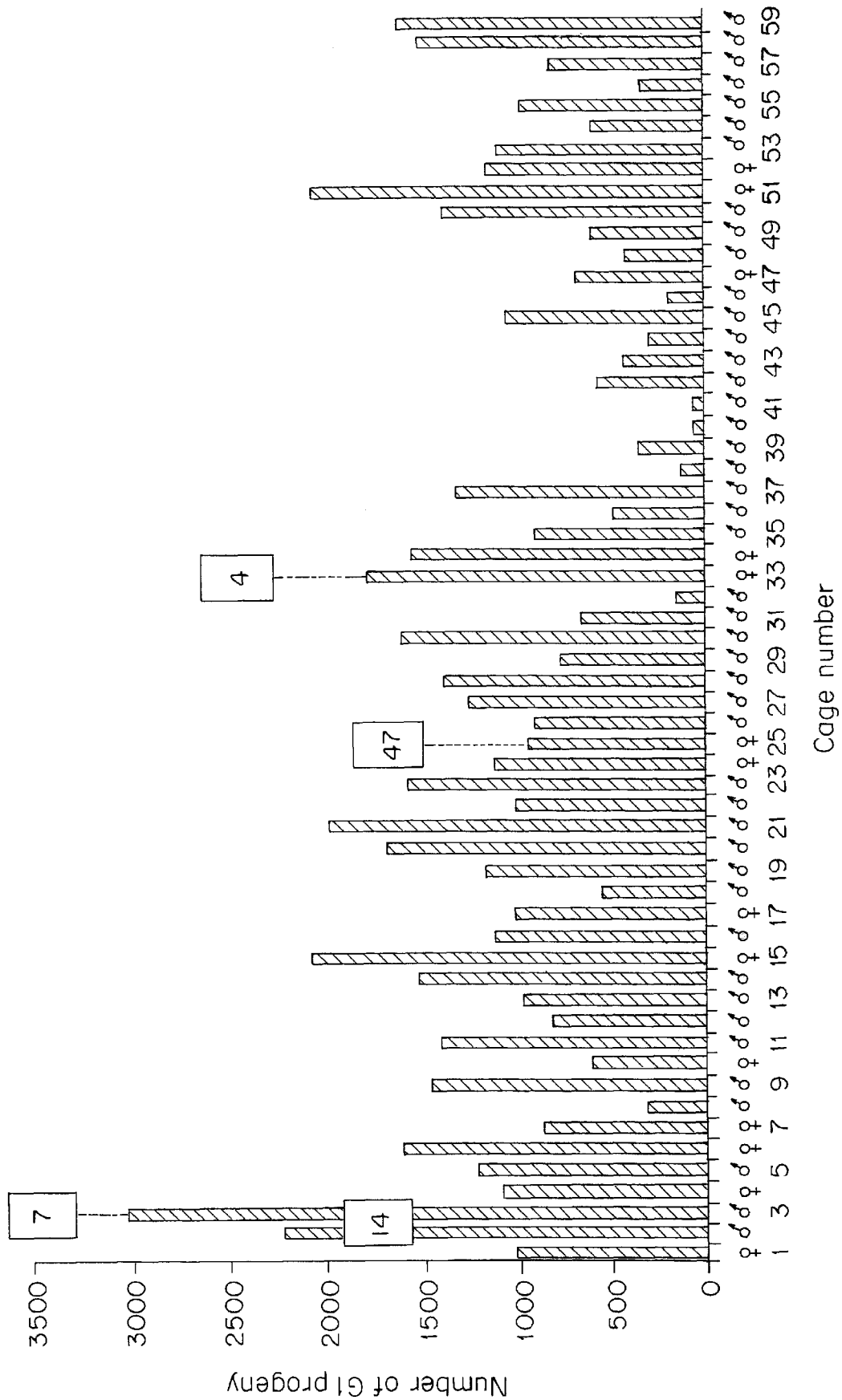
FIG. 4 is a bar graph depicting the frequencies of transformants among G1 progeny. Bars indicate the numbers of G1 flies from the individual cages. The sex of the G0 flies in each cage is indicated. The numbers above cages 1, 3, 25 and 33 indicate the $w^+$ flies that were recovered from these cages.

A total of 3,998 embryos were injected. After injection, they were left to hatch under halocarbon oil, and first instar larvae were transferred to Petri dishes containing standard larval food (Mintzas, A. C. et al., *Dev. Biol.* 95: 492 (1983)). The 390 adults (G0 generation) resulting from injected embryos were collected within 12 hours after eclosion and back-crossed to w flies in small groups consisting of either 5 G0 males and 10 virgin w females, or 10 G0 females and 5 w males. Fifty-nine such G0 groups were reared in small plastic cages and the G1 progeny were collected and handled separately for each group. To induce expression of the w mini-gene from the Hsp70 promoter, G1 pupae were exposed daily to a 39° C. heat shock for one hour. The 62,510 G1 flies that were produced were screened for the presence of non-white eye phenotypes. As shown in FIG. 4, a total of 72 flies with colored eyes were recovered from four different cages.

The w mini-gene gives partial reversion of the phenotype. Eye color varies in strength among different transformants. The phenotype is dosage-dependent with homozygotes having stronger colors than heterozygotes. These characteristics of w markers are useful in sorting multiple insertions and in distinguishing homozygous from heterozygous transformants. The characteristics are due to low levels of expression combined with chromosomal position effects and have been observed previously in Drosophila.

To establish transformed lines, individual G1's were initially back-crossed to w flies. Single pairs of transformed G2 progeny were then mated, and their homozygous G3 progeny, recognized by their stronger $w^+$ phenotypes, were used to construct homozygous lines. Table 3 shows the results from the G1 back-crosses. In these crosses, the non-white eye ($w^+$) phenotype was inherited as a single, dominant trait.

To determine the effect of temperature on the expression of the w mini-gene, a number of G2 pupae were not subjected to the heat shock treatment. When compared to the heat-shocked cohort, G2 flies which had not been heat shocked as pupae showed either paler eye color or no eye color at all; the only exception was lines 3.1 and 3.3, which exhibited an invariant strong yellow eye phenotype. The heat shock dependence clearly showed that the flies (perhaps with the exception of 3.1 and 3.3) were true transformants, rather than revertants of the w mutation.

In cages 3 and 25, differences in the eye color phenotypes of individual G1's from the same cage were detected and bred true, suggesting that independent transformation events had occurred in the same cage.

TABLE 3

| G1 | Eye color of heterozygotes | White heat shock | | Without heat shock | | Eye color of homozygotes |
|---|---|---|---|---|---|---|
|  |  | non-white eyes | white eyes | non-white eyes | white eyes |  |
| 1.1 | pale yellow | 46 | 53 | 0 | 59 | apricot |
| 1.8 | pale yellow | 220 | 274 | 0 | 77 | apricot |
| 1.12 | pale yellow | 94 | 69 | 0 | 8 | apricot |
| 3.1 | yellow | 267 | 237 | 110 | 97 | yellow |
| 3.3 | yellow | 225 | 214 | 53 | 49 | yellow |
| 3.2 | pale yellow | 132 | 118 | 0 | 76 | apricot |
| 3.6 | pale yellow | 70 | 81 | 0 | 81 | apricot |
| 25.7 | pale apricot | 119 | 156 | 116* | 91 | apricot |
| 25.8 | pink | 24 | 18 | 0 | 27 | peach |
| 25.9 | pink | 30 | 34 | 0 | 9 | peach |
| 33.2 | pale orange | 42 | 50 | ND | ND | orange |
| 33.3 | pale orange | 29 | 31 | ND | ND | orange |
| 33.4 | pale orange | 16 | 15 | ND | ND | orange |

*Eye color much weaker than with heat shock.

To determine the nature of the integration events, DNA from transformants was analyzed by Southern blot hybridizations using several restriction enzymes and two probes (see FIG. 3A), one (M) containing the Minos sequences at the ends of the transposon (which are not present in non-transformed Medfly), and another (W) containing an internal fragment of the w cDNA sequences (which is present in the endogenous w gene).

Adult genomic DNA (approximately 10 μg per lane) was digested with a restriction endonuclease, subjected to agarose gel electrophoresis, blotted onto nitrocellulose membrane filters and hybridized with $^{32}$P-labeled probes. Membranes were pre-hybridized for 6 hours at 65° C. in 7% SDS, 0.5M phosphate buffer pH 7.4, 1 mM EDTA. Hybridization was for 12–14 hours at 65° C. in 7% SDS, 0.5M phosphate buffer pH 7.4, 1 mM EDTA. Excess probe was removed by two 10-minute washes with 5% SDS, 40 mM phosphate buffer pH 7.4, 1 mM EDTA at 65° C. followed by a 20-minute wash at room temperature with the same buffer pre-warmed at 65°.

Figure 3B:
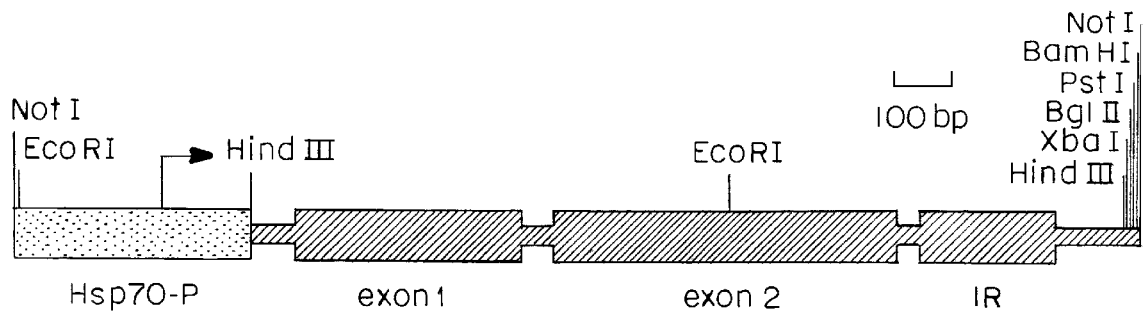
FIG. 3B is a diagram of the insert of the Minos helper plasmid pHSS6hsMi. Speckled box indicates the *D. melanogaster* Hsp70 promoter (Hsp70-P) sequence. Salient restriction sites are shown. Exon 1 and exon 2 are also referred to herein as open reading frame 1 (ORF1) and open reading frame 2 (ORF2), respectively. IR indicates the right-hand terminal inverted repeat.

DNA from lines 3.1, 3.2, 3.3 and 3.6 was cut with SalI and hybridized with a 1 kb HhaI fragment containing Minos sequences present in pMiNot (M probe of FIG. 3A).

DNA from the recipient w strain and from lines 3.1, 3.2, 3.3 and 3.6 was cut with HincII, and probed with a SalI/XhoI fragment containing 1.5 kb of Medfly w cDNA sequences (W probe of FIG. 3A) and with the M probe. Between the two hybridizations the filter was dehybridized by washing with boiling 0.5% SDS solution for 2 minutes.

In Drosophila, insertions of elements like Minos can occur at many different chromosomal sites, and are characterized by precise integration extending through the terminal inverted repeats of the element without transposition of any flanking plasmid DNA. The results of M-hybridized SalI digests document that the events in the Medfly are of the same nature. The transposon has inserted variable host DNA sites, and no significant (>0.2 kb) flanking plasmid DNA to the right of the transposon can be present, because this would have been signaled by the presence of a 2.9 kb band. The results also confirm that two independent events have occurred in cage 3, one represented by lines 3.1 and 3.3 and the other by lines 3.2 and 3.6 (cf. Table 3). These conclusions were also confirmed with HincII digests. Similarly, blots of HincII digests hybridized with the W probe showed the two endogenous w gene bands, plus a third novel band that is characteristic of the insertion event (3.1/3.3 or 3.2/3.6). The shortest band is longer than the 1.9 kb band that would have been expected if the HincII site, 0.2 kb to the right of the Minos end (see FIG. 3A) had been present. The same HincII blot hybridized with the M probe showed that the shortest band is longer than the 1.1 kb band that would have been expected if plasmid sequences to the left of the transposon were present. These results were confirmed with W-hybridized SalI digests.

To assess the integrity of the internal part of the transposon, restriction analysis using EcoRI was performed in three lines derived from cage 25. DNA from strains 25.7, 25.8 and 25.9 was cut with EcoRI and hybridized with the W and M probe sequentially. In addition to the transformants showing non-white eye phenotypes white-eyed siblings (25.9-w, 25.8-w, 25.7-w) were included in this analysis. The results of the hybridization with the W probe indicate that the entire 3.7 kb fragment containing the Hsp70/w marker fusion is present in the w⁺ transformants. Hybridization of the same filter with the M probe, which detects "chimeric" end fragments, showed that lines 25.8 and 25.9 contain the same, single insertion of the transposon. The pattern in 25.7 is consistent with the presence of two insertions, neither identical to the 25.8/25.9 event. One of these insertions, defined by the ~3 kb and ~5.5 kb bands, is also present in the white-eyed siblings of the 25.7 flies. This, presumably, represents a "silent" insertion that does not express the phenotype either due to an undetected lesion in the transposon, or because the transposon has integrated into a silent (perhaps heterochromatic) genomic region.

Restriction analysis of the transformants revealed that, as predicted by the phenotypes (Table 3), two independent transformants were represented among the G1 progeny of cage 3, two in cage 25, and one in cage 33 (Data for transformants from cage 33 are not shown. The restriction patterns of three G1's from cage 1 were identical to these of the 3.2/3.6 event. Evidently, a G0 male present in cage 3 had mated with a G0 female of cage 1, before the G0 flies were sorted into cages.) Only one of these 5 transformants (25.7) had a second (phenotypically silent) event in the same germ line. The different transformants from the same cages are derived either from single or multiple G0 parents. The overall frequency of phenotypically detectable transformation events (5/390 G0 adults) is sufficient for producing several transformants from a single experiment since thousands of embryos can be injected and hundreds of G0 adults can be obtained within a week using a relatively simple experimental setup.

To confirm the presence of a single Minos insertion in transformant 3.1, third instar larva salivary gland polytene chromosomes were prepared and in situ hybridization were performed essentially as described previously (Zacharopoulou, A., et al., *Chromosoma* 101: 448 (1992)). The 3.7 kb NotI fragment containing the Hsp70/w minigene fusion was used as probe. Hybridization to polytene chromosomes of salivary glands from transformed third instar larvae confirmed the presence of single Minos insertions, allowing their cytological localization.

Equivalents

Those skilled in the art will recognize or be able to ascertain, using no more than routine experimentation, many equivalents to the specific embodiments of the invention described herein. Such equivalents are intended to be encompassed by the following claims.

What is claimed is:

1. An isolated transposable element having a DNA sequence which hybridizes to the DNA sequence of SEQ ID NO:1 or SEQ ID NO:4 in a buffered solution of 0.9M NaCl, at a temperature of 55° C.

2. The isolated transposable element of claim 1 having a nucleotide sequence selected from the group consisting of: SEQ ID NO:4, SEQ ID NO:6 and SEQ ID NO:8.

3. An isolated DNA sequence which encodes a transposase protein, or an active portion of a transposase protein, the isolated DNA sequence being characterized by the ability to hybridize to the DNA sequence of SEQ ID NO:1 or SEQ ID NO:4 in a buffered solution of 0.9M NaCl, at a temperature of 55° C.

4. The isolated DNA sequence of claim 3 having a nucleotide sequence selected from the group consisting of: SEQ ID NO:4, SEQ ID NO:6 and SEQ ID NO:8.

5. The isolated DNA sequence of claim 3 which encodes an amino acid sequence selected from the group consisting of: SEQ ID NO:5, SEQ ID NO:7 and SEQ ID NO:9.

* * * * *